United States Patent [19]

McCoy et al.

[11] Patent Number: 5,635,182

[45] Date of Patent: *Jun. 3, 1997

[54] METHOD OF DETECTING LIGAND INTERACTIONS

[75] Inventors: John M. McCoy, Reading; Zhijian Lu, Arlington, both of Mass.

[73] Assignee: Genetics Institute, Inc., Cambridge, Mass.

[*] Notice: The portion of the term of this patent subsequent to Dec. 14, 2010, has been disclaimed.

[21] Appl. No.: 260,582

[22] Filed: Jun. 16, 1994

[51] Int. Cl.$^6$ .................. A61K 39/00; C12N 15/62; C12N 15/00

[52] U.S. Cl. .................. 424/192.1; 424/93.2; 435/252.3; 435/252.31; 435/252.33; 435/254.11; 435/697; 435/172.3; 530/327; 530/330; 530/350; 536/23.1; 536/23.4; 935/79; 935/80

[58] Field of Search .................. 536/23.4, 23.1; 530/350, 330, 327; 435/172.3, 252.3, 252.31, 354.11, 252.33, 240.1, 69.7; 424/93.2, 192.1; 935/79, 80

[56] References Cited

U.S. PATENT DOCUMENTS

| | | | |
|---|---|---|---|
| 4,801,536 | 1/1989 | Stahl et al. | 435/69.1 |
| 5,270,181 | 12/1993 | McCoy et al. | 435/69.7 |
| 5,292,466 | 3/1994 | McCoy et al. | 435/69.7 |
| 5,292,646 | 3/1994 | McCoy et al. | 435/69.7 |
| 5,457,038 | 10/1995 | Trinchieri et al. | 435/69.52 |

FOREIGN PATENT DOCUMENTS

| | | |
|---|---|---|
| 0237045A2 | 3/1987 | European Pat. Off. . |
| WO92/13955A1 | 8/1992 | WIPO . |
| WO93/20846 | 10/1993 | WIPO . |
| WO94/02502A1 | 2/1994 | WIPO . |

OTHER PUBLICATIONS

Gubler et al. 1991 Proc. Natl. Acad. Sci., USA 88:4143–4147.
Wakasugi et al., Proc. Nat'l. Acad. Sci. U.S.A. 87:8282–8286 (1990).
Bardwell et al., Cell 67:581–589 (1991).
Bennett et al., Nature 334:268–270 (1988).
Mazzarella et al., J. Biol. Chem. 265:1094–1101 (1990).
LaVallie et al., Bio/Technology 11:187–193 (1993).
Ellis et al., Biochemistry 31:4882–91 (1992).
Eklund et al., EMBO J. 3:1443–1449 (1984).
Holmgren, J. Biol. Chem. 264:13963–13966 (1989).
Lim et al., J. Bacteriol. 163:311–316: (1985).
Xia, Protein Science 1:310–321 (1992).
Maniatis et al., Molecular Cloning. A Laboratory Manual. (1982) Cold Spring Harbor Laboratory.
Smith, Science 228:1315–1317 (1985).
Scott et al., Science 249:386–390 (1990).
Parmley et al., Gene 73:305–318 (1988).
Djojonegoro et al., Bio/Technology 12:169–172 (1994).
Oldenberg et al., Proc. Nat'l. Acad. sci. U.S.A. 89:5393–5397 (1992).
Scott et al., Proc. Nat'l. Acad. Sci. U.S.A. 89:5398–5402 (1992).
Blond–Elguindi et al., Cell 75:717–728 (1993).
Hammer et al., J. Exp. Med. 176:1007–1013 (1992).

(List continued on next page.)

Primary Examiner—Robert A. Wax
Assistant Examiner—Gabriele E. Bugalsky
Attorney, Agent, or Firm—M. C. Meinert

[57] ABSTRACT

Provided by the present invention are novel methods of detecting ligand interactions, as well as regents useful in the method, including DNA and host cells; and more specifically relates to novel methods for the detection of protein/protein interactions and their application in epitope mapping and the study of ligand/receptor interactions. Also provided are vaccines and kits comprising the expression products and host cells of the invention.

28 Claims, 7 Drawing Sheets

OTHER PUBLICATIONS

Wilson et al., Can. J. Microbiol. 39:451–472 (1993).
Joys, Can J. Microbiol. 34:452–458 (1988).
Sanger et al., J. Mol. Biol. 162:729–773 (1982).
Edman et al., Nature 317:267–270 (1985).
Brent et al., Proc. Nat'l. Acad. Sci. 78:4204–4208 (1981).
Russell et al., J. Bacteriol. 171:2614–2618 (1989).
Hamilton et al., J. Bacteriol. 171:4617–4622 (1989).
Blair et al., J. Bacteriol. 173:4049–4055 (1991).
Norrander et al., Gene 26:101–106 (1983).
Newton et al. "Expression and immunogenicity of a streptococcal M protein epitope inserted in *Salmonella flagelin*" Infection and Immunity 59: 2158–2165.
Yu et al. "Identification and nu8cleotide sequence of the activator gene of the externally induced phosphoglycerate transport system of *Salmonella typhimurium*" Gene 45: 51–57.
Revell et al. "Nucleotide sequence and expression in *Escherichia coli* of cDNAs encoding papaya proteinase omega from *Carica papaya*". Gene 127:221–225.
Toh et al. "The 60–to 90–kDa parietal cell autoantigen associated with autoimmune gastritis is a β subunit of the gastric H+/K+–ATPase (proton pump)". Proceedings of the National Academy of Sciences, USA 87: 6418–6422.
Stocker, "Aromatic–dependent Salmonella as live vaccine presenters of foreign epitopes as inserts in flagelin" Res. Microbiol 141: 787–796.

FIGURE 1.0

```
   1 GACGAAAGGG CCTCGTGATA CGCCTATTTT TATAGGTTAA TGTCATGATA
  51 ATAATGGTTT CTTAGACGTC AGGTGGCACT TTTCGGGGAA ATGTGCGCGG
 101 AACCCCTATT TGTTTATTTT TCTAAATACA TTCAAATATG TATCCGCTCA
 151 TGAGACAATA ACCCTGATAA ATGCTTCAAT AATATTGAAA AAGGAAGAGT
 201 ATGAGTATTC AACATTTCCG TGTCGCCCTT ATTCCCTTTT TGCGGCATT
 251 TTGCCTTCCT GTTTTGCTC ACCCAGAAAC GCTGGTGAAA GTAAAGATG
 301 CTGAAGATCA GTTGGGTGCA CGAGTGGGTT ACATCGAACT GGATCTCAAC
 351 AGCGGTAAGA TCCTTGAGAG TTTTCGCCCC GAAGAACGTT TTCCAATGAT
 401 GAGCACTTTT AAAGTTCTGC TATGTGGCGC GGTATTATCC CGTATTGACG
 451 CCGGGCAAGA GCAACTCGGT CGCCGCATAC ACTATTCTCA GAATGACTTG
 501 GTTGAGTACT CACCAGTCAC AGAAAAGCAT CTTACGGATG CATGACAGT
 551 AAGAGAATTA TGCAGTGCTG CCATAACCAT GAGTGATAAC ACTGCGGCCA
 601 ACTTACTTCT GACAACGATC GGAGGACCGA AGGAGCTAAC CGCTTTTTTG
 651 CACAACATGG GGGATCATGT AACTCGCCTT GATCGTTGGG AACCGGAGCT
 701 GAATGAAGCC ATACCAAACG ACGAGCGTGA CACCACGATG CCTGTAGCAA
 751 TGGCAACAAC GTTGCGCAAA CTATTAACTG GCGAACTACT TACTCTAGCT
 801 TCCCGGCAAC AATTAATAGA CTGGATGGAG GCGGATAAAG TTGCAGGACC
 851 ACTTCTGCGC TCGGCCCTTC CGGCTGGCTG GTTTATTGCT GATAAATCTG
 901 GAGCCGGTGA GCGTGGGTCT CGCGGTATCA TTGCAGCACT GGGGCCAGAT
 951 GGTAAGCCCT CCCGTATCGT AGTTATCTAC ACGACGGGGA GTCAGGCAAC
1001 TATGGATGAA CGAAATAGAC AGATCGCTGA GATAGGTGCC TCACTGATTA
1051 AGCATTGGTA ACTGTCAGAC CAAGTTTACT CATATATACT TTAGATTGAT
1101 TTAAAACTTC ATTTTTAATT TAAAAGGATC TAGGTGAAGA TCCTTTTTGA
1151 TAATCTCATG ACCAAAATCC CTTAACGTGA GTTTTCGTTC CACTGAGCGT
1201 CAGACCCCGT AGAAAGATC AAAGGATCTT CTTGAGATCC TTTTTTTCTG
1251 CGCGTAATCT GCTGCTTGCA ACAAAAAAA CCACCGCTAC CAGCGGTGGT
```

FIGURE 1.1

```
1301 TTGTTTGCCG GATCAAGAGC TACCAACTCT TTTTCCGAAG GTAACTGGCT
1351 TCAGCAGAGC GCAGATACCA AATACTGTCC TTCTAGTGTA GCCGTAGTTA
1401 GGCCACCACT TCAAGAACTC TGTAGCACCG CCTACATACC TCGCTCTGCT
1451 AATCCTGTTA CCAGTGGCTG CTGCCAGTGG CGATAAGTCG TGTCTTACCG
1501 GGTTGGACTC AAGACGATAG TTACCGGATA AGGCGCAGCG GTCGGGCTGA
1551 ACGGGGGGTT CGTGCACACA GCCCAGCTTG GAGCGAACGA CCTACACCGA
1601 ACTGAGATAC CTACAGCGTG AGCATTGAGA AAGCGCCACG CTTCCCGAAG
1651 GGAGAAAGGC GGACAGGTAT CCGGTAAGCG GCAGGGTCGG AACAGGAGAG
1701 CGCACGAGGG AGCTTCCAGG GGGAAACGCC TGGTATCTTT ATAGTCCTGT
1751 CGGGTTTCGC CACCTCTGAC TTGAGCGTCG ATTTTGTGA TGCTCGTCAG
1801 GGGGGCGGAG CCTATGGAAA AACGCCAGCA ACGCGGCCTT TTTACGGTTC
1851 CTGGCCTTTT GCTGGCCTTT TGCTCACATG TTCTTTCCTG CGTTATCCCC
1901 TGATTCTGTG GATAACCGTA TTACCGCCTT TGAGTGAGCT GATACCGCTC
1951 GCCGCAGCCG AACGACCGAG CGCAGCGAGT CAGTGAGCGA GGAAGCGGAA
2001 GAGCGCCCAA TACGCAAACC GCCTCTCCCC GCGCGTTGGC CGATTCATTA
2051 ATGCAGAATT GATCTCTCAC CTACCAAACA ATGCCCCCCT GCAAAAAATA
2101 AATTCATATA AAAAACATAC AGATAACCAT CTGCGGTGAT AAATTATCTC
2151 TGGCGGTGTT GACATAAATA CCACTGGCGG TGATACTGAG CACATCAGCA
2201 GGACGCACTG ACCACCATGA AGGTGACGCT CTTAAAAATT AAGCCCTGAA
2251 GAAGGGCAGC ATTCAAAGCA GAAGGCTTTG GGGTGTGTGA TACGAAACGA
2301 AGCATTGGCC GTAAGTGCGA TTCCGGATTA GCTGCCAATG TGCCAATCGC
2351 GGGGGGTTTT CGTTCAGGAC TACAACTGCC ACACACCACC AAAGCTAACT
2401 GACAGGAGAA TCCAGATGGA TGCACAAACA CGCCGCCGCG AACGTCGCGC
2451 AGAGAAACAG GCTCAATGGA AAGCAGCAAA TCCCTGTTG GTTGGGGTAA
2501 GCGCAAAACC AGTTCCGAAA GATTTTTTA ACTATAAACG CTGATGGAAG
2551 CGTTTATGCG GAAGAGGTAA AGCCCTTCCC GAGTAACAAA AAAACAACAG
```

FIGURE 1.2

```
2601 CATAAATAAC CCCGCTCTTA CACATTCCAG CCCTGAAAAA GGGCATCAAA

2651 TTAAACCACA CCTATGGTGT AGTAATCAAC GACTTGCAAT ATAGGATAAC

2701 GAATC ATG GCA CAA GTC ATT AAT ACC AAC AGC CTC TCG CTG
        1▶Met Ala Gln Val Ile Asn Thr Asn Ser Leu Ser Leu

2742 ATC ACT CAA AAT AAT ATC AAC AAG AAC CAG TCT GCG CTG
   13▶Ile Thr Gln Asn Asn Ile Asn Lys Asn Gln Ser Ala Leu

2781 TCG AGT TCT ATC GAG CGT CTG TCT TCT GGC TTG CGT ATT
   26▶Ser Ser Ser Ile Glu Arg Leu Ser Ser Gly Leu Arg Ile

2820 AAC AGC GCG AAG GAT GAC GCA GCG GGT CAG GCG ATT GCT
   39▶Asn Ser Ala Lys Asp Asp Ala Ala Gly Gln Ala Ile Ala

2859 AAC CGT TTC ACC TCT AAC ATT AAA GGC CTG ACT CAG GCG
   52▶Asn Arg Phe Thr Ser Asn Ile Lys Gly Leu Thr Gln Ala

2898 GCC CGT AAC GCC AAC GAC GGT ATC TCC GTT GCG CAG ACC
   65▶Ala Arg Asn Ala Asn Asp Gly Ile Ser Val Ala Gln Thr

2937 ACC GAA GGC GCG CTG TCC GAA ATC AAC AAC AAC TTA CAG
   78▶Thr Glu Gly Ala Leu Ser Glu Ile Asn Asn Asn Leu Gln

2976 CGT GTG CGT GAA CTG ACG GTA CAG GCC ACT ACC GGT ACT
   91▶Arg Val Arg Glu Leu Thr Val Gln Ala Thr Thr Gly Thr

3015 AAC TCT GAG TCT GAT CTG TCT TCT ATC CAG GAC GAA ATT
  104▶Asn Ser Glu Ser Asp Leu Ser Ser Ile Gln Asp Glu Ile

3054 AAA TCC CGT CTG GAT GAA ATT GAC CGC GTA TCT GGT CAG
  117▶Lys Ser Arg Leu Asp Glu Ile Asp Arg Val Ser Gly Gln

3093 ACC CAG TTC AAC GGC GTG AAC GTG CTG GCA AAA AAT GGC
  130▶Thr Gln Phe Asn Gly Val Asn Val Leu Ala Lys Asn Gly

3132 TCC ATG AAA ATC CAG GTT GGC GCA AAT GAT AAC CAG ACT
  143▶Ser Met Lys Ile Gln Val Gly Ala Asn Asp Asn Gln Thr

3171 ATC ACT ATC GAT CTG AAG CAG ATT GAT GCT AAA ACT CTT
  156▶Ile Thr Ile Asp Leu Lys Gln Ile Asp Ala Lys Thr Leu

3210 GGC CTT GAT GGT TTT AGC GTT AAA AAT AAC GAT ACA GTT
  169▶Gly Leu Asp Gly Phe Ser Val Lys Asn Asn Asp Thr Val

3249 ACC ACT AGT GCT CCA GTA ACT GCT TTT GGT GCT ACC ACC
  182▶Thr Thr Ser Ala Pro Val Thr Ala Phe Gly Ala Thr Thr

3288 ACA AAC AAT ATT AAA CTT ACT GGA ATT ACC CTT TCT ACG
  195▶Thr Asn Asn Ile Lys Leu Thr Gly Ile Thr Leu Ser Thr

3327 GAA GCA GCC ACT GAT ACT GGC GGA ACT AAC CCA GCT TCA
  208▶Glu Ala Ala Thr Asp Thr Gly Gly Thr Asn Pro Ala Ser
```

FIGURE 1.3

```
3366 ATT GAG GGT GTT TAT ACT GAT AAT GGT AAT GAT TAC TAT
 221▶Ile Glu Gly Val Tyr Thr Asp Asn Gly Asn Asp Tyr Tyr

3405 GCG AAA ATC ACC GGT GGT GAT AAC GAT GGT ATG AGC GAT
 234▶Ala Lys Ile Thr Gly Gly Asp Asn Asp Gly Met Ser Asp

3444 AAA ATT ATT CAC CTG ACT GAC GAC AGT TTT GAC ACG GAT
 247▶Lys Ile Ile His Leu Thr Asp Asp Ser Phe Asp Thr Asp

3483 GTA CTC AAA GCG GAC GGG GCG ATC CTC GTC GAT TTC TGG
 260▶Val Leu Lys Ala Asp Gly Ala Ile Leu Val Asp Phe Trp

3522 GCA GAG TGG TGC GGT CCG TGC AAA ATG ATC GCC CCG ATT
 273▶Ala Glu Trp Cys Gly Pro Cys Lys Met Ile Ala Pro Ile

3561 CTG GAT GAA ATC GCT GAC GAA TAT CAG GGC AAA CTG ACC
 286▶Leu Asp Glu Ile Ala Asp Glu Tyr Gln Gly Lys Leu Thr

3600 GTT GCA AAA CTG AAC ATC GAT CAA AAC CCT GGC ACT GCG
 299▶Val Ala Lys Leu Asn Ile Asp Gln Asn Pro Gly Thr Ala

3639 CCG AAA TAT GGC ATC CGT GGT ATC CCG ACT CTG CTG CTG
 312▶Pro Lys Tyr Gly Ile Arg Gly Ile Pro Thr Leu Leu Leu

3678 TTC AAA AAC GGT GAA GTG GCG GCA ACC AAA GTG GGT GCA
 325▶Phe Lys Asn Gly Glu Val Ala Ala Thr Lys Val Gly Ala

3717 CTG TCT AAA GGT CAG TTG AAA GAG TTC CTC GAC GCT AAC
 338▶Leu Ser Lys Gly Gln Leu Lys Glu Phe Leu Asp Ala Asn

3756 CTG GCC TGT GCC GCC AGT TCT CCA ACC GCG GTC AAA CTG
 351▶Leu Ala Cys Ala Ala Ser Ser Pro Thr Ala Val Lys Leu

3795 GGC GGA GAT GAT GGC AAA ACA GAA GTG GTC GAT ATT GAT
 364▶Gly Gly Asp Asp Gly Lys Thr Glu Val Val Asp Ile Asp

3834 GGT AAA ACA TAC GAT TCT GCC GAT TTA AAT GGC GGT AAT
 377▶Gly Lys Thr Tyr Asp Ser Ala Asp Leu Asn Gly Gly Asn

3873 CTG CAA ACA GGT TTG ACT GCT GGT GGT GAG GCT CTG ACT
 390▶Leu Gln Thr Gly Leu Thr Ala Gly Gly Glu Ala Leu Thr

3912 GCT GTT GCA AAT GGT AAA ACC ACG GAT CCG CTG AAA GCG
 403▶Ala Val Ala Asn Gly Lys Thr Thr Asp Pro Leu Lys Ala

3951 CTG GAC GAT GCT ATC GCA TCT GTA GAC AAA TTC CGT TCT
 416▶Leu Asp Asp Ala Ile Ala Ser Val Asp Lys Phe Arg Ser

3990 TCC CTC GGT GCG GTG CAA AAC CGT CTG GAT TCC GCG GTT
 429▶Ser Leu Gly Ala Val Gln Asn Arg Leu Asp Ser Ala Val

4029 ACC AAC CTG AAC AAC ACC ACT ACC AAC CTG TCT GAA GCG
 442▶Thr Asn Leu Asn Asn Thr Thr Thr Asn Leu Ser Glu Ala
```

FIGURE 1.4

```
4068 CAG TCC CGT ATT CAG GAC GCC GAC TAT GCG ACC GAA GTG
 455▶Gln Ser Arg Ile Gln Asp Ala Asp Tyr Ala Thr Glu Val

4107 TCC AAT ATG TCG AAA GCG CAG ATC ATC CAG CAG GCC GGT
 468▶Ser Asn Met Ser Lys Ala Gln Ile Ile Gln Gln Ala Gly

4146 AAC TCC GTG TTG GCA AAA GCT AAC CAG GTA CCG CAG CAG
 481▶Asn Ser Val Leu Ala Lys Ala Asn Gln Val Pro Gln Gln

4185 GTT CTG TCT CTG CTG CAG GGT TAA TCGTTGTAAC CTGATTAACT
 494▶Val Leu Ser Leu Leu Gln Gly ···

4229 GAGACTGACG GCAACGCCAA ATTGCCTGAT GCGCTGCGCT TATCAGGCCT

4279 ACAAGTTGAA TTGCAATTTA TTGAATTTGC ACATTTTTGT AGGCCGGATA

4329 AGGCGTTTAC GCGCATCCGG CAACATAAAG CGCAATTTGT CAGCAACGTG

4379 CTTCCCGCCA CCGGCGGGGT TTTTTCTGC CTGGAATTTA CCTGTAACCC

4429 CCAAATAACC CCTCATTTCA CCCACTAATC GTCCGATTAA AAACCCTGCA

4479 GAAACGGATA ATCATGCCGA TAACTGCTAT AACGCAGGGC TGTTTNNNNN

4529 NNNNNNNGAA TTCCCGGGGA TCCTCTAGAG TCGACCTGCA GGCATGCAAG

4579 CTTGGCACTG GCCGTCGTTT TACAACGTCG TGACTGGGAA AACCCTGGCG

4629 TTACCCAACT TAATCGCCTT GCAGCACATC CCCCTTTCGC CAGCTGGCGT

4679 AATAGCGAAG AGGCCCGCAC CGATCGCCCT TCCCAACAGT TGCGCAGCCT

4729 GAATGGCGAA TGGCGCCTGA TGCGGTATTT TCTCCTTACG CATCTGTGCG

4779 GTATTTCACA CCGCATATAT GGTGCACTCT CAGTACAATC TGCTCTGATG

4829 CCGCATAGTT AAGCCAGCCC CGACACCCGC CAACACCCGC TGACGCGCCC

4879 TGACGGGCTT GTCTGCTCCC GGCATCCGCT TACAGACAAG CTGTGACCGT

4929 CTCCGGGAGC TGCATGTGTC AGAGGTTTTC ACCGTCATCA CCGAAACGCG

4979 CGA
```

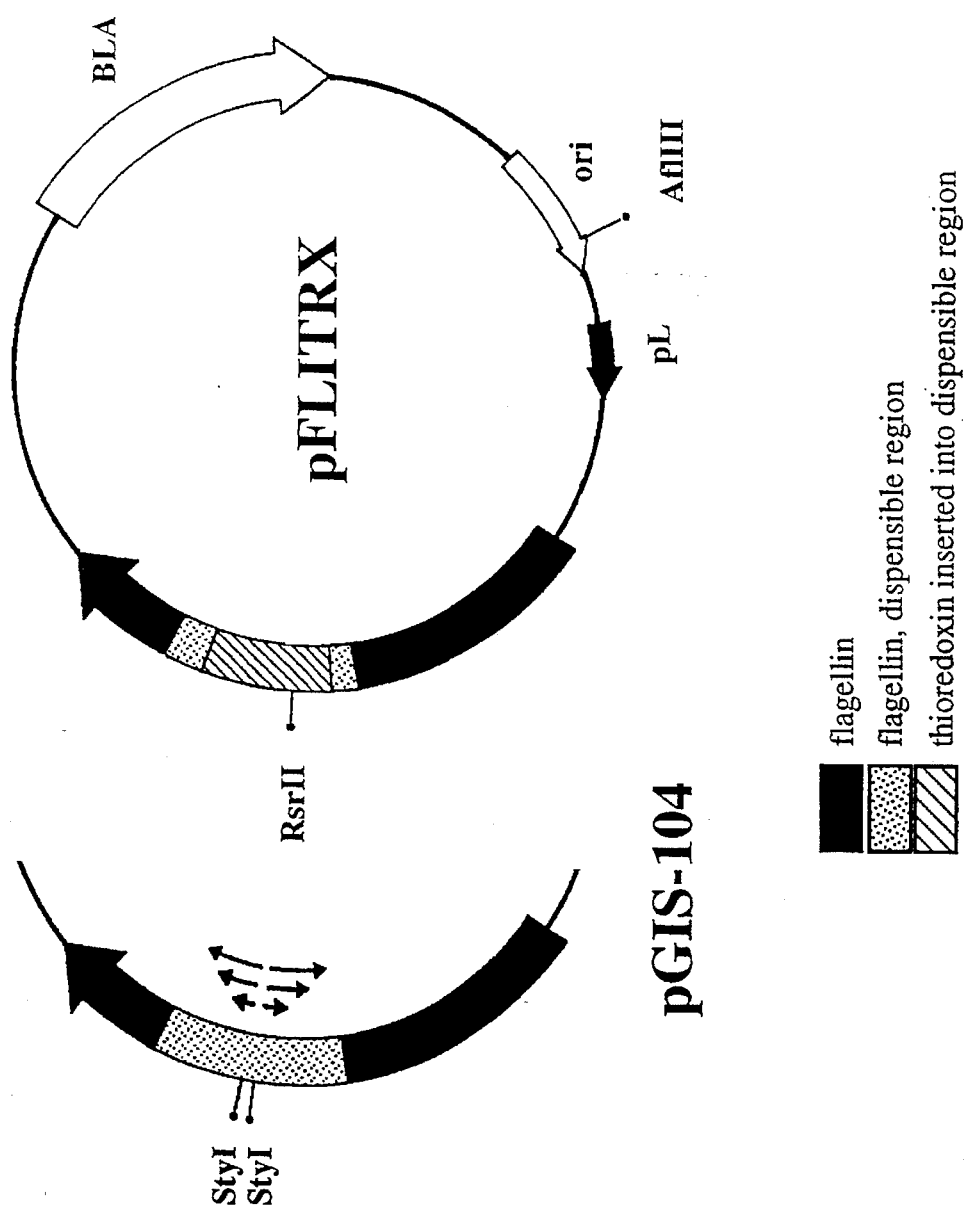

FIGURE 3

RANDOM PEPTIDE INSERTIONS INTO THE ACTIVE-SITE
LOOP OF E.COLI THIOREDOXIN (trxA)

```
                              RsrII
                              |
                ....GAGTGGTGCGGTCCGTGCAAAATG....
   trxA active  ---------------------------------
   site loop
                ....CTCACCACGCCAGGCACGTTTTAC....

....E  W  C  G  P  C  K  M  ....
                    31                    38
```

```
              ....GAGTGGTGCG        GTCCGTGCAAAATG....
   RsrII cut  -----------           --------------
              ....CTCACCACGCCAG        GCACGTTTTAC....

....E  W  C  G          P  C  K  M ....
                  31                           38
```

```
                  (AvaII)              AvaII
            5'      |                    |           3'
                 GACTGACTGGTCCG...(N36)...GGTCCTCAGTCAGTCAG
   oligos    ----------------------------------------------
                                         CCAGGAGTCAGTCAGTC
                              3'                          5'
```

```
   random              GTCCG...(N36)...G
   duplex              ------------------
                          GC...(N36)...CCAG
``` insertion into trxA active site loop

```
            ....GAGTGGTGCGGTCCG...(N36)...GGTCCGTGCAAAATG....
            ----------------------------------------------
            ....CTCACCACGCCAGGC...(N36)...CCAGGCACGTTTTAC....

....E  W  C  G  P..(X12)..G  P  C  K  M  ....
                31                                   38
```

METHOD OF DETECTING LIGAND INTERACTIONS

FIELD OF INVENTION

The present invention relates generally to novel methods of detecting ligand interactions, useful in detecting proteins and peptides, as well as reagents useful in the method, including DNA and host cells; and more specifically relates to novel methods for the detection of protein/protein interactions and their application in epitope mapping and the study of ligand/receptor interactions.

BACKGROUND OF THE INVENTION

Understanding the interactions between macromolecules is a central theme of biology, with complementarity in the surface character and shape of these molecules usually defining both the specificity and strength of their interactions. Traditionally, the best method of precisely defining these contact surfaces is to determine the tertiary structure of an interacting complex by X-ray diffraction or by multi-dimensional NMR techniques. However, these approaches are not always technically feasible, are very costly, and can be time consuming. Easier methods for helping to define interacting surfaces at the molecular level could prove extremely useful, for instance in the exploration of protein-protein contacts involved in receptor/ligand interactions, in understanding the basis of enzyme/substrate specificities, and in the mapping of antibody epitopes, to name just a few examples. However, a formidable obstacle to be overcome in the development of such new techniques is the tremendous structural diversity of biological macromolecules.

Recently a method has been successfully pioneered by Smith and others (Smith, Science 228:1315–1317 (1985); Scott et al., Science 249:386–390 (1990); and Parmley et al., Gene 73:305–318 (1988)) that enables screening of huge populations of diverse macromolecules, and selecting specific members of these populations on the basis of their binding affinity to an immobilized protein target molecule. In this technique, termed the phage-display method, DNA sequences encoding highly diverse libraries of short peptides are fused to the 5'-ends of bacteriophage coat protein genes. Following expression, these fusions are correctly folded and assembled, exposing the random peptides on the bacteriophage surface. The phage/peptide libraries are then given the opportunity to bind to a target immobilized protein, typically a monoclonal antibody, and phage displaying peptides that interact specifically with the target are selectively retained through a washing procedure. The retained phage particles are then eluted for additional rounds of selections or for analyses.

Since its introduction, the phage-display technique and its variations have been applied to map a wide range of protein-protein or protein-ligand interactions (Djojonegoro et al., BioTechnology 12:169–172 (1994); Oldenberg et al., Proc. Nat'l. Acad. Sci. U.S.A. 89:5393–5397 (1992); Scott et al., Proc. Nat'l Acad. Sci U.S.A. 89:5398–5402 (1992); Blond-Elguindi et al., Cell 75:717–728 (1993); and Hammer et al., J. Exp. Med. 176:1007–1013 (1992)). The peptide sequence information derived from these studies is useful, but the ability to perform structural studies on the peptides obtained is limited both by the low expression levels of phage coat protein genes and by the character of the peptides selected by these systems, which are usually unconstrained molecules possessing many degrees of conformational freedom. This structural flexibility renders difficult any subsequent structural studies on these molecules.

Also of background interest to the present invention is Stahl et at., U.S. Pat. No. 4,801,536; issued Jan. 31, 1989; incorporated by reference, which disclose that C-terminal fusions of peptides and proteins to flagellin can be made and exported from the cell. Unfortunately, such fusions do not assemble into functional or even partially functional flagella. McCoy et al., U.S. Pat. No. 5,292,646; issued Mar. 8, 1994; incorporated by reference, discloses that both N- and C-terminal fusions of peptides and proteins to thioredoxin can be made. However, these fusion proteins reside in the bacterial cytoplasm, i.e., on the interior of the cell. Furthermore, while fusions of a wide variety of peptide sequences were shown by McCoy et at., supra, to be permissible into the active-site loop of thioredoxin and without deleterious effects on thioredoxin protein folding; nevertheless, these active-site loop fusions also reside in the bacterial cytoplasm.

Accordingly, there continues to be a need in the art for alternative methods and reagents which address these problems.

BRIEF SUMMARY OF THE INVENTION

Provided by the present invention are methods and reagents for detecting ligand interactions. These methods are useful in identifying and characterizing both known and novel proteins and peptides, as well as identifying and characterizing the ligand(s) with which they interact.

According to the methods of the present invention, peptides are displayed on the surface of a cell. These peptides, either of designed or random sequence, are displayed within the structural content of a peptide-conformation-constraining protein, such as a thioredoxin-like protein. The peptide-conformation-constraining protein is displayed on the exterior of the cell as a fusion to a flagellin-like sequence. Display of the peptides on the surface enables screening against target molecules (candidate interactors) for possible interaction and binding affinity.

In one aspect of the invention, protein/protein interactions are probed using flagella to display random peptide libraries and/or designed peptides on the surface of a flagellate bacterium such as E. coli, C. crescentus, and B. subtilis. A method is provided for detecting a peptide interaction with a target molecule by contacting a host cell with a target molecule and assaying the interaction. The host cell is suitably transformed with a DNA comprising a DNA encoding a thioredoxin-like sequence, a DNA encoding a flagellin-like sequence, and a DNA encoding a peptide. The host cells can be either motile or non-motile and optionally may be modified by introducing a gene, such as motB, or modified to carry cI, and/or specific deletions in their fliC genes. Optionally, a population of host cells can be generated comprising host cells displaying libraries of random and/or biased peptide sequences. In one embodiment, E. coli thioredoxin (trxA) is inserted into a dispensable region of flagellin (fliC). The resulting fusion protein, termed FLITRX, is exported and assembled into a flagellum exposed on the cell surface. A random peptide library, e.g., a FLITRX library, (or a designed peptide) is displayed as conformationally-constrained insertions into the thioredoxin active-site loop. Members of the library are selected via interactions with a target molecule. The target molecules can be either soluble or insoluble, mobile or immobile. The interactions include typical ligand interactions, for example, antigen/antibody; ligand/receptor; enzyme/substrate/cofactor; interacting pairs of transcriptional factors and cell-cycling factors; neurotransmitter/receptor pairs; etc. The methodology allows, for example, for the mapping of antibody epitopes. Optionally, once an interacting target molecule has been identified, it is possible to repeat the method using the same or new peptides or the same or new target molecules to identify potential effector molecules.

Reagents provided by the invention include the DNA constructs, expression products, modified host cells, and transformed host cells and progeny of such cells. The DNA constructs include a DNA encoding a thioredoxin-like sequence and a DNA encoding a flagellin-like sequence, and further encoding random or designed peptide sequences. Optionally included in the constructs are linker sequences and sequences encoding cleavage sites. The peptides can be anywhere from 1 to 60 amino acids, and more, in length. The peptide sequence can be within the thioredoxin-like and/or the flagellin-like sequence. A presently preferred construct is FLITRX (FIG. 1 and SEQ ID NO:76). Other preferred constructs include those of SEQ ID NOS: 6–40, 42–63 and 65–72. The corresponding expression products of the DNA constructs are also provided. Presently preferred expression products include those of SEQ ID NOS:6–40 and 73.

Also provided by the invention are vaccines comprising the expression products or the host cells (and progeny) of the invention. Further provided are kits comprising, for example, a FLITRX library or further comprising the host cells (and progeny) of the invention.

DESCRIPTION OF THE SEQUENCE ID NOS. AND FIGURES

Other aspects and advantages of the present invention will be apparent upon consideration of the following detailed description hereof which includes numerous illustrative examples of the practice of the invention, with reference being made to the following SEQ ID NOS. and figure:

SEQ ID NO: 1 is not used.

SEQ ID NOS:76 and 77 provide the nucleotide sequence, and the corresponding amino acid sequence, for the FLITRX construct and comprises E. coli trxA and fliC.

SEQ ID NO:2 is PLC-20, a 20 residue peptide from bovine phospholipase C-II.

SEQ ID NOS:3 and 4 correspond to oligos 1 and 2.

SEQ ID NO:5 is a non-specific peptide.

SEQ ID NOS:6–40 correspond to peptides 8-1 to 8-35 (Table 1); and SEQ ID NO:41 provides a partial amino acid sequence for IL-8 (Table 1).

SEQ ID NOS:42–63 correspond to peptides M-1 to M-22 (Table 2); and SEQ ID NO:64 provides a partial amino acid sequence for M-CSF (Table 2).

SEQ ID NOS:65–71 correspond to peptides 12-1 to 12-7 (Table 3); and SEQ ID NO:72 provides a partial amino acid sequence for p40 of hIL-12 (Table 3).

SEQ ID NOS: 73, 74 and 75, provide the consensus amino acid sequences, respectively, for the epitopes of antibodies to IL-8, M-CSF, and IL-12 (Example 4, page 31).

FIGS. 1.0–1.4 provide a 4981 nucleotide sequence, and the corresponding amino acid sequence, for FLITRX, comprising E. coli thioredoxin (trxA) and E. coli flagellin (fliC). (SEQ ID NOS:76 and 77).

FIG. 2 provides plasmid maps tier the flagellin expression vector pGIS-104 and the thioredoxin-flagellin fusion vector pFLITRX. The dispensable region of flagellin is shown, the arrows indicate the area where deletions are made within this dispensable region to find a suitable position to insert thioredoxin.

FIG. 3 is a schematic drawing illustrating random peptide insertions, where N is any nucleotide and X is any amino acid, into the active-site loop of E. coli thioredoxin (trxA).

DETAILED DESCRIPTION OF THE INVENTION

The present invention provides methods and reagents useful for detecting protein-protein interactions and useful in identifying novel proteins and peptides. According to the method of the present invention, random (or designed) peptides are displayed, on the surface of a suitable cell, within the structural context of a peptide-conformation-constraining protein, such as, but not limited to, a thioredoxin-like molecule. The thioredoxin or conformation-constraining protein is itself displayed on the exterior of the cell as a fusion to a flagellin-like sequence. Flagellin is the major structural component of the bacterial flagellum.

The tertiary structure of thioredoxin reveals that its active-site sequence, -CGPC-, forms a tight, disulfide-constrained, omega loop on the protein's surface. Previous work has shown that this loop is a highly permissive site for the insertion of a wide variety of peptide sequences, and that these insertions generally do not compromise thioredoxin folding. The inserted sequences are conformationally constrained, tethered at both ends by the tight and stable tertiary fold of thioredoxin itself. Thioredoxin active-site loop peptide fusions can be readily made at very high expression levels, i.e., at least 20%, and up to 40% of the cell's total protein, facilitating structural analyses. Because peptides are displayed on the surface of thioredoxin, it is possible to screen against target molecules (candidate interactors) for binding affinity. The system can be used to map epitopes of antibodies and to study and define other types of protein-protein interactions, as well as molecules that enhance or compete with such particular interactions. Target molecules can be in solution, or bound to supports, or on cell surfaces, etc.

More specifically, the present invention provides a system for probing protein/protein interactions which makes use of the flagellum to display random peptide libraries or designed peptides on the surface of a flagellate bacterium such as E. coli. Flagellin, the major structural protein found in E. coil flagella, is known to contain a large, solvent-exposed, non-essential domain. Deletions within this domain, or indeed of the entire domain, are well-tolerated as judged by retention of at least limited flagellar function. In developing the system, the entire coding sequence of E. coli thioredoxin (trxA) is inserted into a dispensable region of the gene for flagellin (fliC), the major structural component of the E. coli flagellum. The resulting fusion protein (FLITRX) is efficiently exported and assembled into partially functional flagella on the bacterial cell surface. A diverse library of random dodecapeptides are displayed in FLITRX on the exterior of E. coli as conformationally-constrained insertions into the thioredoxin active-site loop, a location which is known to be a highly permissive site for insertion of exogenous peptide sequences in native thioredoxin. Members of this library, also referred to herein as the "FLITRX library", are selected via specific protein/protein interactions; according to one of the methods of the invention, those bacteria displaying peptides with affinity e.g., to immobilized antibodies, can be efficiently isolated. The methodology also allows for unambiquous mapping of distinguishable/unique antibody epitopes. Peptides selected as FLITRX active-site fusions retain their binding specificity when made as native thioredoxin active-site loop fusions.

This facilitates future structural characterizations and broadens the general utility of the system as kits and the like for exploring other classes of protein-protein interactions.

A surprising aspect of the present invention is that by fusing thioredoxin into the interior of flagellin not only can it be exported to the outside of the bacterium, but it also becomes incorporated and assembled into a functional organelle that remains tethered to the cell, i.e., as an exterior, attached, structure.

Also provided by the invention are reagents useful in the practice of the methodology. These reagents include DNA constructs comprising flagellin-like and thioredoxin-like sequences, as well as, constructs comprising random or designed peptide sequences. The sequence of one such construct, FLITRX, is set forth in FIG. 1 (SEQ ID NOS:76 and 77) and comprises a thioredoxin-like sequence and a flagellin-like sequence. Also described is utilization of host cells, such as GI724, and strains with described modifications.

As used herein, flagellin fusions, termed FLIPP, include any sequence encoding a non-flagellin peptide or protein inserted into the flagellin-like sequence and includes FLITRX, where thioredoxin has been inserted into the flagellin-like sequence. Where the peptide of interest has been inserted into the thioredoxin-like sequence portion of FLITRX, the term FLITRXPEP is used and includes, for example, the sequences of Tables 1, 2, and 3. While internal fusion constructs are presently preferred, also useful in the present invention are any fusions which will result in the assembly of a flagellin-like organelle which displays the desired peptide on the exterior. The term "fusion protein" is used herein to include any of the above constructs, e.g., FLIPP, FLITRX, FLITRXPEP, as well as variations thereof.

The invention also provides host cells that have been modified by introducing a gene, such as motB, which causes a flagellar paralysis by physically de-coupling flagellar rotation from attachment to the host cell wall. This modification enhances the binding of the cell, via the fusion protein, to the antibody. In addition, host cells can be modified to carry cI, the bacteriophage λ repressor protein, so that they may serve as suitable hosts for pL-promoter expression plasmids. Optionally, the strains may carry specific deletions in their fliC gene. Also provided are transformed host cells that have been transformed with the above-described DNA constructs.

As used herein, the term "host cell" includes, but is not limited to, cells having the capacity to generate flagella, i.e., organelles used by diverse species to move towards environments that generally promote their survival; and includes types of bacteria known as flagellates. The host cell can be either a non-motile or motile flagellate as long as the capacity to assemble the organelle is retained. Exemplary flagellates include, but are not limited to, *E. coli*, *C. crescentus*, and *B. subtilis*.

The flagellar filament is made up of several thousand self-assembling protein (flagellin) monomers which are arranged in a helix and form a hollow tube, which in turn forms a macrohelical (corkscrew) form. An excellent review article is Wilson, et al., Bacterial flagellar filaments and their component flagellins, Can. J. Microbiol. 39:451 (1993), incorporated by reference, which also lists a variety of suitable species of flagellates (Table 1 and Table 2). Page 462 provides a comparative chart (FIG. 8) setting forth the amino acid sequences that have been published for the 29 flagellins listed in Table 2, page 457. Thus, as used herein, the term "flagellin-like" is meant to encompass such published sequences. As can be seen from FIGS. 7, 8 and 10 of Wilson et al., the bacterial flagellins share significant homologies with each other, particularly at their N- and C-termini. As used herein, the term "flagellin-like" also includes those sequences having at least 25% homology with the N-terminal 80 residues of *E. coli* flagellin or 30% homology to the C-terminal 80 residues and preferably greater than 40% and includes the protein subunit of the flagellar filaments from any flagellated microorganism and other filamentous structures having an appropriately suitable architecture.

DNA sequences which hybridize to the sequence for *E. coli* flagellin or its structural homologs under either stringent or relaxed hybridization conditions also encode flagellin-like proteins for use in this invention. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C. Examples of non-stringent hybridization conditions are 4×SSC at 50° C. or hybridization with 30–40% formamide at 42° C. The use of all such flagellin-like sequences are encompassed by the present invention. See also, Joys, Can. J. Microbiol. 34:452 (1988) and Stahl and LaVallie, U.S. Pat. No. 4,801,536; issued Jan. 31, 1989, both incorporated by reference. The *B. subtilis* hag gene referred to in U.S. Pat. No. 4,801,536 is a close homologue to the fliC of *E. coli*.

Suitable host cells for the invention may be selected from a wide range of flagellate bacterial species including for example *E. coli*., *Caulobacter crescentus*, and *B. subtilis*. The host cell must contain a known or identifiable nucleotide sequence encoding a flagellin protein. It should be noted that bacteria in which flagellin-encoding DNA has not been identified heretofore may also be useful in the practice of this invention. In that case the appropriate nucleotide sequence may be identified and characterized by using conventional techniques to recover and appropriately purify a suitable amount of flagellin from the bacteria for protein sequencing, determine the amino acid sequence of a portion of the flagellin, prepare oligonucleotide probes corresponding to the amino acid sequence so determined, screen a DNA library derived from the bacteria for the presence of a nucleotide sequence capable of hybridizing to the probe(s) and determine the nucleotide sequence of the DNA so identified and/or its location in the bacterial genome. For example, the flagellin gene of *B. subtilis* may be routinely obtained from the *B. subtills* genome as a 2.5 Kb PstI fragment by purely conventional means using an oligonucleotide probe complementary to part or all of the sequence depicted in FIG. 8 of Wilson et al. Similarly, the *E. coli* flagellin gene may be obtained from the *E. coli* Genetic Stock Center, (Barbara Bachmann, Curator, Department of Human Genetics, Yale University, 333 Cedar Street, New Haven, Conn.), on a Clark and Carbon library plasmid, pLC24-16. Part or all of the gene may be routinely identified by hybridization to an oligonucleotide complimentary to the sequence depicted in FIG. 8 of Wilson et al. (or FIG. 1 herein). Alternatively, flagellin genes may be isolated using appropriate oligonucleotides in the polymerase chain reaction.

Preferably, the flagellin gene employed in the practice of this invention should be a native flagellin gene of the bacterial species to be used for expression. However, in certain embodiments, the flagellin gene may be derived from a bacterial species different from that of the cells to be used for expression. Thus, an *E. coli* flagellin gene may be utilized with a *B. subtilis* host cell. The wild-type host cell must contain at least one flagellum and preferably, as in the case of *B. subtilis* or *E. coli*, a plurality of flagella.

A thioredoxin-like sequence is defined herein as a sequence encoding a protein or fragment of a protein characterized by an amino acid sequence having at least 30% homology with the amino acid sequence of *E. coli* thioredoxin corresponding to nucleotide 3435 to 3761 (amino acids 246 to 352) of pFLITRX (SEQ ID NO:76). Alternatively, a thioredoxin-like sequence is defined herein as a sequence encoding a protein or fragment of a protein characterized by having a three dimensional structure substantially similar to that of human or *E. coli* thioredoxin and optionally by containing an active-site loop. The DNA sequence of glutaredoxin is an example of a thioredoxin-like DNA sequence which encodes a protein that exhibits such substantial similarity in three-dimensional conformation and contains a Cys . . . Cys active site loop. The amino acid sequence of *E. coli* thioredoxin is described in H. Eklund et al., EMBO J. 3:1443–1449 (1984). The three-dimensional structure of *E. coli* thioredoxin is depicted in FIG. 2 of A. Holmgren, J. Biol. Chem. 264:13963–13966 (1989). In FIG. 1, nucleotides 3435 to 3761 correspond to a DNA sequence encoding the *E. coli* thioredoxin protein (Lira et al., J. Bacteriol., 163:311–316 (1985)) (SEQ ID NO:76). A comparison of the three dimensional structures of *E. coli* thioredoxin and glutaredoxin is published in Xia, Protein Science I:310–321 (1992). These four publications are incorporated herein by reference for the purpose of providing information on thioredoxin-like proteins that is known to one of skill in the art.

As the primary example of a thioredoxin-like protein useful in this invention, *E. coli* thioredoxin has the following characteristics. *E. coli* thioredoxin is a small protein, only 11.7 kD, and can be produced to high levels (>10%, corresponding to a concentration of 15 µM if cells are lysed at 10 $A_{550}$/ml). *E. coli* thioredoxin is further characterized by a very stable, tight structure which can minimize the effects on overall structural stability caused by fusions to desired peptides or proteins.

The three dimensional structure of *E. coli* thioredoxin is known and contains several surface loops, including a distinctive Cys . . . Cys active-site loop between residues $Cys_{33}$ and $Cys_{36}$ which protrudes from the body of the protein. This Cys . . . Cys active-site loop is an identifiable, accessible surface loop region and is not involved in any interactions with the rest of the protein that contribute to overall structural stability. It is therefore a good candidate as a site for peptide insertions. Both the amino- and carboxyl-termini of *E. coli* thioredoxin are on the surface of the protein, and are readily accessible for fusions. Human thioredoxin, glutaredoxin and other thioredoxin-like molecules also contain this Cys . . . Cys active-site loop.

*E. coli* thioredoxin is also stable to proteases. Thus, *E. coli* thioredoxin may be desirable for use in *E. coli* expression systems, because as an *E. coli* protein it is characterized by stability to *E. coli* proteases. *E. coli* thioredoxin is also stable to heat up to 80° C. and to low pH.

Other thioredoxin-like proteins encoded by thioredoxin-like DNA sequences useful in this invention share homologous amino acid sequences, and similar physical and structural characteristics. Thus, DNA sequences encoding other thioredoxin-like proteins may be used in place of *E. coli* thioredoxin according to this invention. Human thioredoxin has a three-dimensional structure that is virtually superimposable on *E. coli*'s three-dimensional structure, as determined by comparing the NMR structures of the two molecules. Human thioredoxin also contains an active-site loop structurally and functionally equivalent to the Cys . . . Cys active-site loop found in the *E. coli* protein. Accordingly, human thioredoxin is a thioredoxin-like molecule and can be used in place of or in addition to *E. coli* thioredoxin in the production of a FLITRX protein in accordance with the method of this invention. Insertions into the human thioredoxin active-site loop may be as well tolerated as those in *E. coli* thioredoxin.

Other thioredoxin-like sequences which may be employed in this invention include all or portions of the protein glutaredoxin and various species' homologs thereof. (A. Holmgren, supra.) Although *E. coli* glutaredoxin and *E. coli* thioredoxin share less than 20% amino acid homology, the two proteins do have conformational and functional similarities (Eklund et al., EMBO J. 3:1443–1449 (1984)) and glutaredoxin contains an active-site loop structurally and functionally equivalent to the Cys . . . Cys active-site loop of *E. coli* thioredoxin. Glutaredoxin is therefore a thioredoxin-like molecule as herein defined.

The DNA sequence encoding protein disulfide isomerase (PDI), particularly those portions thereof containing the thioredoxin-like domains, and its various species' homologs (J. E. Edman et al., Nature 317:267–270 (1985)) may also be employed as a thioredoxin-like DNA sequence, since a repeated domain of PDI shares>30% homology with *E. coli* thioredoxin and that repeated domain contains an active-site loop structurally and functionally equivalent to the Cys . . . Cys active-site loop of *E. coli* thioredoxin. These three publications are incorporated herein by reference for the purpose of providing information on glutaredoxin and PDI which is known and available to one of skill in the art.

Similarly the DNA sequence encoding phosphoinositide-specific phospholipase C (PIPLC), particularly fragments thereof and various species' homologs thereof (C. F. Bennett et al., Nature 334:268–270 (1988)) may also be employed in the present invention as a thioredoxin-like sequence based on their amino acid sequence homology with *E. coli* thioredoxin, or alternatively based on similarity in three-dimensional conformation and the presence of an active-site loop structurally and functionally equivalent to the Cys . . . Cys active-site loop of *E. coli* thioredoxin. All or a portion of the DNA sequence encoding an endoplasmic reticulum protein, such as ERp72, or various species homologs thereof are also included as thioredoxin-like DNA sequences for the purposes of this invention (R. A. Mazzarella et al., J. Biol. Chem. 265:1094–1101 (1990)) based on amino acid sequence homology, or alternatively based on similarity in three-dimensional conformation and the presence of an active-site loop structurally and functionally equivalent to the Cys . . . Cys active-site loop of *E. coli* thioredoxin. Another thioredoxin-like sequence is a DNA sequence which encodes all or a portion of an adult T-cell leukemia-derived factor (ADF) or other species homologs thereof (N. Wakasugi et al., Proc. Natl. Acad. Sci. USA 87:8282–8286 (1990)). ADF is now believed to be human thioredoxin. Similarly, the protein responsible for promoting disulfide bond formation in the periplasm of *E. coli*, the product of the dsbA gene (J. C. Bardwell et al., Cell 67:581–589 (1991), also can be considered a thioredoxin-like sequence. These four publications are incorporated herein by reference for the purpose of providing information on PIPLC, ERp72, ADF, and dsbA which are known and available to one of skill in the art.

It is expected from the definition of thioredoxin-like sequence used above that other sequences not specifically identified above, or perhaps not yet identified or published, may be thioredoxin-like sequences either based on the 30% amino acid sequence homology to *E. coli* thioredoxin or based on having three-dimensional structures substantially similar to *E. coli* or human thioredoxin and having an active-site loop functionally and structurally equivalent to the Cys . . . Cys active-site loop of *E. coli* thioredoxin. One skilled in the art can determine whether a molecule has these latter two characteristics by comparing its three-dimensional structure, as analyzed for example by x-ray crystallography or 2- dimensional NMR spectroscopy, with the published three-dimensional structure for *E. coli* thioredoxin and by analyzing the amino acid sequence of the molecule to determine whether it contains an active-site loop that is structurally and functionally equivalent to the Cys . . . Cys active-site loop of *E. coli* thioredoxin. By "substantially similar" in three-dimensional structure or conformation is meant as similar to *E. coli* thioredoxin as is glutaredoxin. In addition, a predictive algorithm has been described which enables the identification of thioredoxin-like proteins via computer-assisted analysis of primary sequence (L. B. Ellis et al, Biochemistry 31:4882–91 (1992)). Based on the above description, one of skill in the art will be able to select and identify, or, if desired, modify, a thioredoxin-like DNA sequence for use in this invention without resort to undue experimentation. For example, simple point mutations made to portions of native thioredoxin or native thioredoxin-like sequences which do not effect the structure of the resulting molecule are alternative thioredoxin-like sequences, as are allelic variants of native thioredoxin or native thioredoxin-like sequences.

DNA sequences which hybridize to the sequence for *E. coli* thioredoxin or its structural homologs under either stringent or relaxed hybridization conditions also encode thioredoxin-like proteins for use in this invention. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C. Examples of non-stringent hybridization conditions are 4×SSC at 50° C. or hybridization with 30–40% formamide at 42° C. The use of all such thioredoxin-like sequences are believed to be encompassed in this invention.

Construction of a fusion sequence of the present invention, which comprises the DNA sequence of a selected or random peptide or protein, a flagellin-like sequence and a thioredoxin-like sequence, employs conventional genetic engineering techniques. See, Sambrook et al., Molecular Cloning. A Laboratory Manual., Cold Spring Harbor Laboratory, Cold Spring Harbor, New York (1989). Fusion sequences may be prepared in a number of different ways. For example, the selected protein or peptide may be fused anywhere within the thioredoxin-like molecule. This fusion of a desired peptide or protein to the thioredoxin-like protein increases the stability of the peptide or protein and also subjects the protein or peptide to conformational constraints. The desired peptide or protein is fused in such a manner that the fusion does not destabilize the native structure of either protein.

It may be preferred for a variety of reasons that peptides be fused within the active-site loop of the thioredoxin-like molecule. The region on the surface of thioredoxin surrounding the active-site loop has evolved, in keeping with the protein's major function as a non-specific protein disulfide oxido-reductase, to be able to interact with a wide variety of other protein surfaces, and so may be especially tolerant to the presence of inserted sequences. In addition the active-site loop region is bounded by segments of strong secondary structure, which provides many advantages for peptide fusions. Any small peptide inserted into the active-site loop of a thioredoxin-like protein is present in a region of the protein which is not involved in maintaining tertiary structure. Therefore the structure of such a fusion protein is stable. Indeed previous work has shown that *E. coli* thioredoxin can be cleaved into two fragments at a position close to the active-site loop, and yet the tertiary interactions stabilizing the protein remain intact.

The active-site loop of *E. coli* thioredoxin has the sequence $NH_2$ . . . $Cys_{33}$-Gly-Pro-$Cys_{36}$ . . . COOH. Fusing a selected peptide with a thioredoxin-like protein in the active-site loop portion of the protein constrains the peptide at both ends, reducing the degrees of conformational freedom of the peptide, and consequently reducing the number of possible alternative structures taken by the peptide. The inserted peptide is bound at each end by cysteine residues, which may form a disulfide linkage to each other as they do in native thioredoxin and further limit the conformational freedom of the inserted peptide. Moreover, this invention places the peptide on the surface of the thioredoxin-like protein. Thus, the invention provides a distinct advantage for use of the peptides in screening for bioactive peptide conformations and other assays by presenting peptides inserted in the active-site loop in this structural context.

Additionally the fusion of a peptide into the loop protects it from the actions of *E. coli* amino- and carboxyl-peptidases. Further, a restriction endonuclease cleavage site RsrII already exists in the portion of the *E. coli* thioredoxin DNA sequence encoding the loop region at precisely the correct position for a peptide gene fusion. See FIG. 3. RsrII recognizes the DNA sequence CGG(A/T)CCG leaving a three nucleotide long 5'-protruding sticky end. DNA bearing the complementary sticky ends will therefore insert at this site in only one orientation. The thioredoxin-like sequence or other conformation constraining polypeptide of this invention, is fused within the flagellin-like sequence at an optimum position determined empirically as described below in Example 1. In the absence of tertiary structural information, a logical choice of this location within flagellin is not possible. However, by employing an empirical screen, one skilled in the art can readily determine a suitable fusion site for any combination of a conformation constraining polypeptide and bacterial flagellin.

A fusion sequence of a thioredoxin-like sequence with a desired protein or peptide sequence according to this invention may optionally contain a linker peptide inserted between the flagellin-like sequence and the thioredoxin-like sequence and optionally between the selected peptide or protein. This linker sequence may encode, if desired, a polypeptide which is selectively cleavable or digestible by conventional chemical or enzymatic methods. For example, the selected cleavage site may be an enzymatic cleavage site. Examples of enzymatic cleavage sites include sites for cleavage by a proteolytic enzyme, such as enterokinase, Factor Xa, trypsin, collagenase, and thrombin. Alternatively, the cleavage site in the linker may be a site capable of being cleaved upon exposure to a selected chemical, e.g., cyanogen bromide, hydroxylamine, or low pH.

Cleavage at the selected cleavage site enables separation of the protein or peptide from the FLITRX fusion protein. The released peptide or protein may then be obtained in purified form, free from any polypeptide fragment of the FLITRX protein to which it was previously linked. The cleavage site, if inserted into a linker useful in the fusion sequences of this invention, does not limit this invention.

Any desired cleavage site, of which many are known in the art, may be used for this purpose.

The optional linker sequence of a fusion sequence of the present invention may serve a purpose other than the provision of a cleavage site. The linker may also be a simple amino acid sequence of a sufficient length to prevent any steric hindrance between flagellin-like and the thioredoxin-like molecule and optionally, the selected peptide or protein. In addition, the linker sequence provides for post-translational modification including, but not limited to, e.g., phosphorylation sites, biotinylation sites, sulfation sites, γ-carboxylation sites, and the like.

The length and amino acid composition of the linker sequence can influence the level of production for particular fusions, both in terms of length and composition of the linker. Whether a particular fusion is sensitive to linker length and/or composition can be readily determined empirically without undue experimentation by one skilled in the art using standard techniques.

This invention is not limited to any specific type of peptide or protein. A wide variety of genes or gene fragments are useful in forming the fusion sequences of the present invention. Any selected, desired DNA sequence could be used and can include any peptide or protein useful for human or veterinary therapy, diagnostic or research applications. For example, hormones, cytokines, growth or inhibitory factors, enzymes, modified or wholly synthetic proteins or peptides can be utilized according to this invention.

When expressing these fusion genes, for example, FLIPP, FLITRX, and FLITRXPEP, the exact growth temperature is an important variable to consider for the production of functional proteins. Some are produced optimally at lower temperatures, and for any particular fusion both the optimum temperature and the optimum period for fusion protein production can be determined empirically in a few simple initial experiments if desired. A broad range of temperatures, in the range of approximately 12° C.–37° C. can be examined, with longer production times (up to 24 h) for lower temperatures and shorter production times (3–4 h) for higher temperatures. The exact optima of the time and temperature is determined empirically without undue experimentation by one skilled in the art using standard techniques.

A variety of DNA molecules incorporating the above-described fusion sequences may be constructed for producing the selected peptide or protein according to this invention. At a minimum a desirable DNA sequence according to this invention comprises a fusion sequence described above, in association with, and under the control of, an expression control sequence capable of directing the expression of the fusion gene in a desired host cell. For example, where the host cell is an *E. coli* strain, the DNA molecule desirably contains a promoter which functions in *E. coli*, a ribosome binding site, and optionally, a selectable marker gene and an origin of replication if the DNA molecule is extrachromosomal. Numerous bacterial expression vectors containing these components are known in the art for bacterial expression, and can easily be constructed by standard molecular biology techniques.

The DNA molecules containing the fusion sequences may be further modified to contain different codons to optimize expression in the selected host cell, as is known in the art. These DNA molecules may additionally contain multiple copies of the thioredoxin-like DNA sequence, with the gene for the constrained polypeptide fused to only one of the DNA sequences, or to all copies of the thioredoxin-like sequence. Since bacterial flagella are composed of multimeric assemblies of flagellin monomers, any peptide appropriately fused to flagellin will be displayed to potential target molecules outside the cell in a multivalent fashion. This may be an advantage in initial screens for interacting polypeptides with weaker binding affinities. However, it may be desirable to subsequently select polypeptides with stronger affinities to the target molecule. For this purpose it may be desired to reduce the valency of the FLIPP/target interaction by co-expressing and diluting FLIPP with wild-type flagellin. An additional possibility is to co-express two or more different FLIPP genes in the same cell to produce combinatorial binding modes. It is also possible to integrate a FLIPP, FLITRX or FLITRXPEP DNA sequence into the chromosome of a selected host.

Host cells suitable for the present invention are preferably bacterial cells having the capacity to assemble flagella. Certain cells, while having the capacity are nevertheless non-motile, but can still be used in the invention. *E. coli* strain GI724, used in the following examples, has been deposited with a United States microorganism depository (ATCC 55151). Both motile and non-motile derivatives of GI724 can be used in the invention, and various other strains of bacteria may also be employed.

To produce the fusions of this invention, the host cell is either transformed with, or has integrated into its genome, a DNA molecule comprising a flagellin-like and thioredoxin-like DNA sequence fused to the DNA sequence of a selected peptide or protein, desirably under the control of an expression control sequence capable of directing the expression of a fusion protein. The host cell is then cultured under known conditions suitable for fusion protein production.

The present invention also provides methods and reagents for screening libraries of random (or designed) peptides for their potential activity, e.g., enzyme inhibitory, hormone/growth factor agonist and hormone/growth factor antagonist activity. Also provided are methods and reagents for the mapping of known protein sequences for regions of potential interest, including receptor binding sites, substrate binding sites, phosphorylation/modification sites, protease cleavage sites, epitopes, and the like.

Bacterial colonies expressing the flagellin-like/thioredoxin-like peptide fusion genes, e.g., FLIPP, FLITRX, FLITRXPEP, may be screened using radio-labelled proteins such as hormones or growth factors as probes, or cells having surface target molecules. Positives arising from this type of screen identify mimics of receptor binding sites and may lead to the design of compounds with therapeutic uses. Alternatively, the screen can be used to better define the parameters of suspected protein/protein interactions, as well as drug effectors. Bacterial colonies expressing flagellin-like/thioredoxin-like/peptide fusion genes, e.g. , FLITRXPEP, may also be screened using antibodies raised against native, active hormones or growth factors, and the like. Positives arising from this type of screen could be mimics of surface epitopes present on the original antigen. Where such surface epitopes are responsible for receptor binding, the 'positive' fusion proteins may be studied further for biological activity.

Additionally, the fusion proteins or fusion peptides of this invention may also be used as antigens in the production of vaccines or in the production of monoclonal and polyclonal antibodies, or recombinant antibodies or chimeric antibodies, generated by known methods for diagnostic, purification or therapeutic use. Studies of thioredoxin-like molecules indicate a possible B cell/T cell growth factor activity (N. Wakasugi et al., supra), which may enhance immune response. Alternatively, antibodies elicited to the fusion sequences may also be useful in the purification of many different fusion proteins.

As used herein, the term "target molecule" includes, but is not limited to, any interacting molecule, e.g., a protein, antagonists or agonists, for example, the IL-6 receptor-ligand pair; the TGF-β receptor-ligand pair; the IL-1 receptor-ligand pair and other receptor-ligand interactors; protein kinase-substrate pairs; interacting pairs of transcriptional factors; interacting components of signal transduction pathways, such as the cytoplasmic domains of certain transmembrane receptors and G-proteins; pairs of interacting proteins involved in cell-cycle regulation, such as p16 and CDK4; as well as neurotransmitter pairs; enzymes and their substrates; and the like.

As used herein, the term "peptide" can include the expression product of DNA libraries (which preferably include at least one hundred different peptide species and more preferably include one thousand, one hundred thousand, or an even greater number of individual species, e.g., $10^8$) and can range from one to sixty or more amino acids in length. These peptides can comprise random or designed sequences.

The following examples illustrate practice of the invention. These examples are for illustrative purposes only and are not intended in any way to limit the scope of the invention claimed. Example I describes the construction of the FLITRX vector. Example 2 describes the development of a panning procedure using the FLITRX vector. Example 3 describes the construction of a library of dodecamer random peptide insertions into the thioredoxin active-site loop of the FLITRX fusion protein. Example 4 describes epitope mapping of three monoclonal antibodies, as listed in Tables 1, 2, and 3. Example 5 relates to valency effects in FLITRX screens. Example 6 describes the use of the methodology to study other protein/protein interactions. Example 7 describes use of the methodology to generate vaccines.

EXAMPLE 1

Construction of the pFLITRX Vector

Bacterial Strains

While the invention is described using particular bacterial strains, as is readily appreciated by one skilled in the art, other strains are similarly useful; preferred are those having the capacity to assemble flagella. All bacterial strains used in this invention are derivatives of *E. coli* K12 strain GI724 (ATCC 55151)(LaVallie et al., Bio/Technology 11:187–193 (1993)), which contains the bacteriophage repressor (cI) gene stably integrated into the chromosomal ampC locus. The cI gene in this strain is under the transcriptional control of a synthetic *Salmonella typhimurium* trp promoter, integrated upstream of cl in ampC. GI724 is a suitable host swain for pL expression vectors, and was derived originally from RB791=W3110 laclqL8. (Brent et al., Proc. Nat'l. Acad. Sci. 78:4204–4208 (1981).)

GI724 is non-motile, neither swimming in liquid culture nor migrating on motility agar plates (per liter: 10 g tryptone, 0.5% glucose, 5 g NaCl, 0.35% agar). Like most laboratory strains the specific lesion in GI724 responsible for its non-motility is unknown. As is readily appreciated by one skilled in the art, simply plating out this strain will result in a spontaneous reversion to a highly motile derivative. GI808 is one such spontaneous revertant and is isolated following six successive rounds of selection on motility agar plates, picking from the leading edge of the zone of migration after each round. GI808 is essentially wild-type with respect to cell motility, i.e., motility is essentially restored. This initial step of selecting a cell with motility ensures a fully competent flagellar filament assembly system.

Strain GI809 is derived from GI808, and carries a specific 512 bp deletion within the flagellin gene (fliC, genbank accession #M14358). The deletion extends between the unique BclI and SpeI sites within fliC. GI809 is non-motile by virtue of this deletion; however, motility can be restored by complementation with a wild-type fliC gene on a plasmid. Many methods in the art can be employed to create this specific deletion, e.g., Russell et al., J. Bact. 171:2614 (1989); Hamilton et al., J. Bact. 171:4617 (1989).

Strain GI826 is a P1 transductant of GI809 carrying both a deletion in the motB gene and a tightly linked marker, eda::Tn10. (Blair et al., J. Bacteriol. 173:4049–4055 (1991).) Since the motB mutation causes flagellar paralysis, GI826 is non-motile even when transformed with a plasmid carrying a wild-type fliC gene.

Construction of the pFLITRX Vector

General Approach

A FLITRXPEP fusion molecule of the present invention was prepared using *E. coli* thioredoxin (trxA) as the thioredoxin-like sequence and *E. coli* flagellin (fliC) as the flagellin-like sequence.

Fusion gene constructions were made using standard DNA manipulation techniques, described extensively by Sambrook, Fritsch and Maniatis, Molecular Cloning. A Laboratory Manual, 2nd edition, Cold Spring Harbor Laboratory, Cold Spring Harbor, N.Y. (1989).

The active-site of *E. coli* thioredoxin consists of a short disulfide-bonded loop protruding from the body of the protein, and is highly permissive for the insertion of a wide variety of peptide sequences. 85% of dodecamer peptides of random sequence inserted in this loop can be expressed as stable and soluble thioredoxin fusion proteins, with the inserted peptides lying on the surface of the protein where they are readily accessible to reagents such as proteases and antibodies.

A central region of the fliC gene can be entirely deleted without abolishing flagellar function. This zone extends almost symmetrically for approximately 200 bp on either side of two closely-spaced StyI sites within the gene. FIG. 2 shows a map of the fliC expression plasmid, pGIS-104, and the location of this dispensable region. Within this zone is selected a suitable segment for replacement by full-length thioredoxin in such a way that flagellar assembly is not severely compromised, and such that the active-site loop of thioredoxin is positioned on the flagellar surface. This enables peptides inserted into the thioredoxin active-site to be displayed on the surface of the host cell, e.g., *E. coli*, and to allow screening of large libraries of such peptides for novel binding affinities.

In the absence of any detailed flagellin structural information, it is necessary to devise a screen to find a suitable position for thioredoxin insertion. pGIS-104 is cleaved with StyI and a continuous spectrum of deletions made that extends approximately 250 bp either side of the two StyI sites. See FIG. 2. The mixture of trimmed pGIS-104 plasmids is then cut at a unique AflII site so that, in a subsequent ligation with a trxA-PLC20 fragment, deletions of every length can recombine independently. The trxA-PLC20 fragment includes the entire thioredoxin coding sequence into which an oligonucleotide encoding 20 residues of bovine phospholipase C-II (PLC) that has been inserted within the active-site loop. The ligation products include a wide variety of internal fusions of trxA-PLC20 into the dispensable section of flagellin.

As the trxA-PLC20 fragment contains no termination codon, a proportion of these ligation products are capable of expressing a tripartite fusion protein; (N-terminal flagellin domain)-(trxA-PLC20)-(C-terminal flagellin domain). While this order is preferred, other arrangements are possible. A subset of these tripartite fusions is competent for export to the cell surface, another subset is capable of assembly into functional flagella, and a further subset can display the thioredoxin-PLC20 peptide in a location within flagellin that is accessible for antibody binding.

To find this last class of fusions, colonies from the transformed ligation mixture are transferred to nitrocellulose filters and probed with an antibody raised against the PLC20 peptide. Clones which bind to the antibody are found at a frequency of approximately 0.1%. Forty such clones are isolated, grown in liquid medium and induced for fusion protein synthesis. The resulting bacterial cultures are examined microscopically and also checked for levels of fusion protein production by SDS-PAGE. Although un-transformed GI809 is absolutely non-motile, approximately half of the forty clones are found to be motile to various degrees. Individual bacteria from certain clones are observed to rotate vigorously on a microscope slide, suggesting that they possess flagella which have become tethered to the glass. Although none of these motile clones exhibit a wild-type "swimming" phenotype, the appearance of limited motility indicates that at some level both export and assembly of the fusion protein does occur. One particular clone is selected both for a high fusion protein production level and for showing the most pronounced rotation when examined under the microscope. Removal of PLC-20 sequences from the plasmid isolated from this clone results in a new plasmid fusion vector, pFLITRX (FIG. 1 and SEQ ID NO:76). A map of pFLITRX is shown in FIG. 2.

The entire sequence of the plasmid expression vector, pFLITRX (SEQ ID NO:76), containing sequences encoding the flagellin/thioredoxin fusion protein FLITRX, is illustrated in FIG. 1 and contains the following principal features:

Nucleotides 1–2060 contain DNA sequences originating from the plasmid pUC-18 (Norrander et al., Gene 26:101–106 (1983)) including sequences containing the gene for β-lactamase which confers resistance to the antibiotic ampicillin in host E. coli strains, and a colE1-derived origin of replication.

Nucleotides 2061–2671 contain DNA sequences of bacteriophage X (Sanger et al., J. Mol. Biol. 162:729–773 (1982)), including the sequences for the major leftward promoter (pL) and its three operator sequences, OL1, OL2 and OL3. The operators are the binding sites for cI repressor protein, intracellular levels of which control the amount of transcription initiation from pL.

Nucleotides 2672–3434 are sequences from the E. coli chromosome including sequences encoding an N-terminal portion of the flagellin (FliC) protein. The flagellin coding sequence begins at residue 2706.

Nucleotides 3435–3761 are sequences encoding E. coli thioredoxin, fused at the 5'-end, in-frame, to the sequences encoding an N-terminal portion of flagellin. An RsrII restriction site, unique in this plasmid, is found at residue 3534. This site lies within the thioredoxin gene at a position corresponding to the thioredoxin active-site loop, and can be used as a site to introduce DNA encoding peptide insertions into thioredoxin. At the 3'-end of the thioredoxin sequences the gene is fused, also in-frame, to sequences encoding a C-terminal portion of flagellin.

Nucleotides 3762–4540 are sequences from the E. coli chromosome including sequences encoding this C-terminal portion of the flagellin (FliC) protein. The flagellin coding sequence ends at residue 4208.

Nucleotides 4541–4981 are DNA sequences derived from pUC-18.

Specific Details pGIS-104 (FIG. 2), is a plasmid vector based on pUC-18 which carries the E. coli fliC coding sequence and ribosome binding site (nucleotides 691–2526, genbank accession #X17440) positioned under the control of the bacteriophage pL promoter. Under the conditions described in Example 2 of U.S. Pat. No. 5,292,646; this plasmid transformed into strain GI724 can direct the synthesis of FliC to approximately 20% of the total cell protein. GI809 (fliC) becomes motile when transformed with pGIS-104. (This is true even when pL is not induced due to slight transcriptional leakage of the pL promoter). pGIS-104 carries two adjacent StyI restriction sites separated by 41 bp within the fliC coding region.

25 µg of StyI-cleaved pGIS-104 was digested with 12.5 units of slow BAL31 nuclease (IBI Inc., New Haven, Conn.) at 30° C. in a reaction volume of 250 µl containing 20 mM Tris-Cl, pH 8.0, 0.6M NaCl, 12.5 mM $MgCl_2$, 12.5 mM $CaCl_2$. Under these conditions, the cut ends of the DNA were trimmed back at a rate of approximately 4 bp/minute. 50 µl aliquots were removed at 5, 10, 20, 40 and 80 minutes and the reaction in each aliquot terminated by the addition of 50 µl of buffer-saturated phenol. The five time-points were combined and digested to completion with AflIII. The resulting DNA fragments in the 1500–1700 and the 3000–3200 size ranges were then purified on a polyacrylamide gel and recovered by electroelution.

pALtrxA-PLC20 (the component parts of which are set forth in SEQ ID NOS:76 and 2) is a plasmid in which an oligonucleotide encoding the PLC20 sequence (above) has been inserted into the E. coli thioredoxin (trxA) gene in plasmid pALtrxA-781 (LaVallie et al., Bio/Technology 11:1187–1193 (1993)). The insertion is made at the unique RsrII site, corresponding to the surface-exposed active-site loop of thioredoxin. pALtrxA-PLC20 is digested with NdeI and SfiI and treated with the large (Klenow) fragment of DNA polymerase I in the presence of excess dNTP's to generate flush ends. The 397 bp DNA fragment carrying the entire thioredoxin coding sequence containing the PLC-20 insert is purified on a polyacrylamide gel and recovered by electroelution. This fragment does not carry a translation termination codon at the 3'-end of the thioredoxin gene.

The thioredoxin-PLC20 fragment and the fragments resulting from the BAL31/AflIII digestions of pGIS-104 are ligated together and transformed into strain GI809, plating out at 32° C. onto CAA/amp50 plates (LaVallie et al., Bio/Technology 11:1187–1193 (1993)). (M9 medium containing 1 mM $MgCl_2$ and supplemented with 0.5% glucose, 2% casamino acids, 50 µg/ml ampicillin and 1.5% agar).

Colonies, approximately 0.5 mm in size, are replica-transferred onto nitrocellulose filters and placed, colony side up, onto CAA/amp50 plates supplemented with 200 µg/ml tryptophan to induce pL. After five hours, the filters are lifted off the agar plates and blocked overnight in TS buffer (50 mM Tris-Cl pH 7.5, 150 mM NaCl) containing 1% nonfat dry milk, 5 mM $MgCl_2$, 0.5 µg/ml DNase I and 20 µg/ml lysozyme. They are then washed three times with TS before a 4 h exposure to a solution comprising TS, 1% nonfat dry milk and a 1:100 dilution of GI808-presorbed Ab-PLC.

Ab-PLC is a rabbit antiserum raised to a 20 residue peptide (PLC20) derived from bovine phospholipase C-II (-QPFEDFRISQEHLADHFDGR-)(SEQ ID NO:2). The antiserum was pre-treated with a lysate of strain GI808 before use. Three further washes with TS are followed by exposure for 1 h to a solution comprising TS, 1% nonfat dry milk and [$^{125}$I]-labelled protein A. Finally filters are washed three times with TS, air dried, and exposed to X-ray film. Positive colonies are selected and analyzed for fusion protein expression and motility as described above.

EXAMPLE 2

Development of a "Panning" Protocol Using the FLITRX Vector

According to the invention, pFLITRX can confer on a transformed strain, e.g., GI809, the ability to bind to an immobilized antibody. For example, several different monoclonal antibodies raised to native *E. coli* thioredoxin are adsorbed as patches onto glass microscope slides, and the ability of bacteria to bind to these patches is examined microscopically. pFLITRX-transformed GI809 is found to bind well to several of these anti-thioredoxin antibodies. Specific binding is observed as a dense patch of individual bacteria rotating vigorously over the area where antibody is applied to the slide. GI809 by itself does not bind, and a monoclonal antibody raised against human EPO does not cause pFLITRX-containing bacteria to adhere to the glass. Nevertheless, a small number of rotating bacteria are always seen on regions of the slide where no antibody is laid down due to non-specific binding. One percent nonfat dry milk and 150 mM NaCl are found to be effective in blocking these non-specific interactions.

In selecting an appropriate thioredoxin antibody, improved results are obtained with antibodies directed to the exposed portions of the thioredoxin molecule. One such thioredoxin monoclonal antibody, TD 1/33.2.1, is chosen for providing a suitable level of binding, and the binding experiment is repeated successfully using plastic tissue culture dishes instead of glass slides. The amount of adsorbed antibody required to saturate a 60 mm tissue culture dish is titrated, and 10 µg of antibody is found to be saturating. Flagella are known to be shear sensitive; thus, bound cells can be quantitatively released from slides or plates by a simple mechanical shock, i.e., merely by vortexing for 30 sec on a high setting. This observation is used later as the basis for the elution step in the selection procedure.

TD 1/33.2.1 immobilized on a tissue culture dish selectively enriches for pFLITRX-transformed cells out of a mixed population of GI809 (un-transformed) and GI809/pFLITRX (transformed). The enrichment for transformed cells is monitored by examining the ratio of ampicillin sensitive to ampicillin resistant cells both before and after selection. Colony morphology routinely changes following enrichment as explained below. Before the enrichment procedure, all colonies, both of GI809 and of pFLITRX/GI809, are of a uniformly large diameter. Following enrichment, the colonies change to a mixed phenotype, with a population of smaller diameter colonies appearing. These small colonies are not an extraneous bacterial contaminant. The mixed morphology is reminiscent of flu, a phenotype in *E. coli* where a spontaneous switch in the orientation of a reversible DNA element causes changes in the expression of fimbrial genes. Fimbriae are surface structures, long filaments which *E. coli* uses to adhere to intestinal epithelia. These filaments exhibit lectin-like binding to the complex carbohydrates found on mammalian glycoproteins such as antibody molecules. Fimbriated *E. coli* grow as small, raised colonies whereas non-fimbriated *E. coli* form larger flat colonies. It is suspected that during the enrichment experiments, a population of fimbriated *E. coli* is selected, adhering to the immobilized antibody via lectin-like interactions, and appearing as the smaller colony class following enrichment. Binding of fimbriae to carbohydrate is known to be inhibited by the presence of D-mannose and its analogs; thus, 1% α-methyl mannoside is included in the binding and wash solutions. Incorporating α-methyl mannoside into the procedure eliminates the appearance of the smaller colonies initially observed following enrichment.

Optionally, the host swain can be further modified by the introduction of motB into GI809, generating the new strain GI826. (See Example 1.) The motB mutation causes a flagellar paralysis by physically uncoupling flagellar rotation from attachment to the cell wall, a situation analogous to putting an automobile transmission into neutral. By preventing flagellar rotation, binding to immobilized antibodies is improved; indeed an approximate 50% increase is observed in the ability to select pFLITRX-containing GI826 from a host strain background when compared to pFLITRX-containing GI809.

A panning procedure was developed for pFLITRX in strain GI826 incorporating all of the modifications discussed above. An example of this procedure is given below. GI826 and pFLITRX-containing GI826 cultures are mixed at a ratio of 20,000:1 in IMC medium (M9 medium containing 1 mM MgCl$_2$ and supplemented with 0.5% glucose, 0.2% casamino acids). Six tissue culture plates, 60 mm in diameter (Nunc, Denmark) are each coated for 1 h with 20 µg of TD1/33.2.1 antibody in 1 ml of sterile water by gentle agitation at 50 rpm on a rotary shaker. TD1/33.2.1 is a murine monoclonal (IgG1) raised to native *E. coli* thioredoxin. The plates are then rinsed with sterile water and blocked for 1 h with IMC medium containing 1% non-fat dry milk, 1% α-methyl mannoside and 0.15M NaCl. The blocking solution is poured off the plates and 10 ml of the GI826/pFLITRX-GI826 mixture is added to each in the presence of a final concentration of 1% non-fat dry milk, 1% α-methyl mannoside, and 0.15M NaCl. The plates are allowed to sit for 1 h.

At the end of that time, the unbound cells are poured off and the plates washed with IMC medium to remove the undesired cells. The desired bacteria are eluted from one plate by vortexing on high for 30 sec, and the others subjected to consecutive washes. After each wash the bacteria are eluted from one additional plate. After six washes all of the eluted samples are checked for the ratio of GI826 to pFLITRX-containing GI826 by examining the growth of eluted bacteria on ampicillin-containing and non-selective media. While the number of pFLITRX-containing GI826 bacteria eluted from the dishes remains fairly constant, the number of eluted host cells decreases dramatically during the washing procedure. After six washes the ratio of GI826 to pFLITRX-containing GI826 changes from 20,000:1 to 3.5:1, an overall selection over the course of the procedure of almost 6,000 fold.

EXAMPLE 3

Construction of a Library of Dodecamer Random Peptide Insertions into the Thioredoxin Active-Site Loop of the FLITRX Fusion Protein FIG. 3 illustrates the strategy of the method. A DNA encoding a peptide of any suitable length, can be used in the invention and can be readily synthesized. In one application, two synthetic oligonucleotides are synthesized as follows:

Oligo 1 is 5'- GACTGACTG*GTCCG(NNN)$_{12}$G*GTCCTCAGTCAGTCAG-3', (SEQ ID NO:3) where N is any nucleotide. (* indicates the cleavage positions of two AvaII sites flanking the central "randomized" region).

Oligo 2 is 5'-CTGACTGACTGAGGACC-3' (SEQ ID NO:4)
and is complementary to the 3'-end of oligo 1. Two nmoles of oligo 2 and 500 pmoles of oligo 1 are annealed together in 100 μl of water by slow cooling to room temperature from 95° C. The mixture is then adjusted to a total reaction volume of 200 μl containing 50 mM Tris-Cl pH 8, 10 mM MgCl$_2$, 1 mM DTT and 400 μM of each of the four deoxynucleotide triphosphates. Ten units of the large (Klenow) fragment of DNA polymerase I are added and the primer extension reaction allowed to proceed at 37° C. for 1 h before it is terminated by the addition of buffer-saturated phenol. The reaction products are cleaved with AvaII before being ligated into dephosphorylated, RsrII-cleaved pFLITRX. The ligation mixture is transformed into strain GI826 by electroporation to generate a library of clones expressing random 12-mer peptides on the E. coli cell surface. The diversity of the library is calculated to be $1.77 \times 10^8$ individual clones.

EXAMPLE 4

Epitope Mapping Using the FLITRX System

The above "panning" procedure is applied to map the epitopes of three murine monoclonal antibodies, HIL8-NR7 (anti-human IL-8), HM7/7.7 (anti-human M-CSF) and C11.5.14 (anti-human IL-12). HILS-NR7 is a neutralizing murine monoclonal (IgG) raised to recombinant human Interleukin-8 and obtained from Devaron Inc. (Dayton, N.J.). HM7/7.7 is a murine monoclonal (IgG2a) raised to recombinant human M-CSF. C11.5.14 is a murine monoclonal (IgG1) raised to recombinant human Interleukin-12 heterodimer. All three antibodies bind to their antigen under reduced and denaturing conditions, suggesting that in each case the antibody epitope is probably a contiguous peptide sequence, as distinguished from a discontinuous or non-linear sequence.

A schematic of the selection procedure is shown in the flow diagram below.

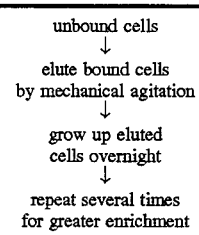

All incubations are performed at 25° C. and all manipulations are at room temperature. An aliquot of the FLITRX random dodecapeptide insert library of Example 3 is grown to saturation for 15 h in IMC/amp100 medium (M9 medium containing 1 mM MgCl$_2$ and supplemented with 0.5% glucose, 0.2% casamino acids and 100 μg/ml ampicillin). Care is taken to ensure that the inoculum for this culture represents at least $2 \times 10^{10}$ cells, i.e., 100× the library diversity, to ensure that all peptides are represented at least once in the final selection. Two ml of this culture ($10^{10}$ cells) are then diluted 1:25 into fresh IMC/amp 100 medium containing 100 μg/ml tryptophan and incubated for an additional 6 h.

In the interim, a 60 mm tissue culture plate (Nunc, Denmark) is coated for 1 h with 20 μg of antibody in 1 ml of sterile water by gentle agitation at 50 rpm on a rotatory shaker. The plate is then rinsed with sterile water and blocked for 1 h with IMC/amp100 medium containing 1% nonfat dry milk, 150 mM NaCl and 1% α-methyl mannoside.

After the induced library culture is incubated for 6 h, it is adjusted to a final concentration of 1% nonfat dry milk, 150 mM NaCl, and 1% α-methyl mannoside. As flagella are very shear sensitive, all subsequent manipulations are performed very gently so as not to shear-the-flagella. The blocking solution is poured off the plate and 10 ml of the induced cells are added. The plate is mixed for one minute by gentle agitation at 50 rpm on a rotatory shaker before being left undisturbed for 1 h on the benchtop. The mixture containing un-bound cells is then gently discarded and the plate carefully washed five times with 10 ml IMC/amp100 medium containing 1% α-methyl mannoside, with each wash constituting five min of gentle rotation with the wash solution at 50 rpm on the shaker. The final washings are poured off and the bound cells eluted into the small volume of residual wash solution by 30 sec of vigorous agitation on a vortexer. Eluted cells are collected by rinsing the plate with 10 ml fresh IMC/amp100 medium and are incubated at 25° C. until reaching saturation. After three successive rounds of binding and washing the FLITRX dodecamer library, using the above antibodies as targets, the selected bacteria are plated on agar growth medium and the strongest "hits" identified using the nitrocellulose filter binding protocol described, supra. Sequences of the selected peptide inserts are listed in Tables 1 through 3.

TABLE 1

The sequences of the "hits" for the IL-8 antibody HIL8-NR7

| | | | | | | | | | | | | | | | | | | | |
|---|---|---|---|---|---|---|---|---|---|---|---|---|---|---|---|---|---|---|---|
| | | V | G | N | T | H | G | R | H | P | K | F | G | | | | | 8-1 -SEQ ID NO: 6 |
| | | | | | | | | W | H | P | K | F | S | L | T | R | G | L | N | 8-2 -SEQ ID NO: 7 |
| | | | | | | | | | H | P | K | F | Y | R | M | I | G | L | E | D | 8-3 -SEQ ID NO: 8 |
| | | | | | | T | L | H | P | K | F | S | I | G | R | Q | G | | | 8-4 -SEQ ID NO: 9 |
| | | G | V | G | E | V | H | P | K | F | L | V | R | | | | | 8-5 SEQ ID NO: 10 |

| | | | | S | T | G | Q | H | R | K | F | D | L | G | R | | | 8-6 SEQ ID NO: 11 |
|---|---|---|---|---|---|---|---|---|---|---|---|---|---|---|---|---|---|---|
| | | R | V | D | A | P | H | R | K | F | M | R | G | | | | | 8-7 SEQ ID NO: 12 |
| | | | | K | V | H | R | K | F | G | S | F | G | R | S | | | 8-8 SEQ ID NO: 13 |
| | I | P | N | T | A | H | R | K | F | P | D | D | | | | | | 8-9 SEQ ID NO: 14 |
| | | S | K | G | P | H | K | K | F | G | V | Y | A | | | | | 8-10 SEQ ID NO: 15 |
| | | R | P | I | P | K | F | R | Y | T | G | | | | | | | 8-11 SEQ ID NO: 16 |
| | | | G | A | H | D | K | F | R | R | A | S | R | I | | | | 8-12 SEQ ID NO: 17 |
| | K | W | R | D | H | D | K | F | S | T | R | N | | | | | | 8-13 SEQ ID NO: 18 |
| S | K | G | R | P | N | T | V | H | S | K | F | | | | | | | 8-14 SEQ ID NO: 19 |
| | K | I | F | E | G | R | V | H | T | K | F | I | | | | | | 8-15 SEQ ID NO: 20 |
| | | Y | G | L | Q | I | P | H | N | K | F | S | R | | | | | 8-16 SEQ ID NO: 21 |
| | G | D | S | D | N | R | M | H | M | K | F | R | | | | | | 8-17 SEQ ID NO: 22 |
| | | | | V | A | N | H | R | K | F | I | G | L | G | Q | | | 8-18 SEQ ID NO: 23 |
| | | | | A | N | I | A | R | K | F | R | A | M | V | E | | | 8-19 SEQ ID NO: 24 |
| | | T | G | M | G | V | H | K | K | F | L | R | F | | | | | 8-20 SEQ ID NO: 25 |
| | G | R | H | G | Q | A | V | H | A | K | F | A | | | | | | 8-21 SEQ ID NO: 26 |
| | Y | R | A | R | E | H | I | H | D | K | F | R | | | | | | 8-22 SEQ ID NO: 27 |
| | | | | | I | P | H | R | K | F | R | Q | L | S | W | V | | 8-23 SEQ ID NO: 28 |
| | | | R | A | H | A | H | S | K | F | P | S | V | E | | | | 8-24 SEQ ID NO: 29 |
| | | | S | T | G | Q | H | R | K | F | D | L | G | R | | | | 8-25 SEQ ID NO: 30 |
| A | S | L | P | G | P | L | H | Q | K | F | L | | | | | | | 8-26 SEQ ID NO: 31 |
| | | | | | | K | H | R | K | F | S | N | V | S | E | F | M | 8-27 SEQ ID NO: 32 |
| | | | | V | S | V | H | S | K | F | A | S | R | K | A | | | 8-28 SEQ ID NO: 33 |

| | | | | V | G | P | H | P | K | H | R | M | V | L | G | | | 8-29 SEQ ID NO: 34 |
|---|---|---|---|---|---|---|---|---|---|---|---|---|---|---|---|---|---|---|
| | R | Q | E | R | L | I | H | P | K | Y | G | I | | | | | | 8-30 SEQ ID NO: 35 |

| | | G | K | G | E | V | H | R | K | H | R | V | G | | | | | 8-31 SEQ ID NO: 36 |
|---|---|---|---|---|---|---|---|---|---|---|---|---|---|---|---|---|---|---|
| | | | | T | I | H | R | K | H | L | Q | R | T | E | G | | | 8-32 SEQ ID NO: 37 |
| | | | G | N | P | H | A | K | R | K | G | S | Q | M | | | | 8-33 SEQ ID NO: 38 |
| E | H | R | P | D | G | Y | H | L | K | F | H | | | | | | | 8-34 SEQ ID NO: 39 |
| T | T | T | G | Q | A | L | A | R | K | F | Y | | | | | | | 8-35 SEQ ID NO: 40 |

10-I K T Y S K P F H P K F I K E L-25 IL-8    SEQ ID NO: 41

TABLE 2

The sequences of the "hits" for the M-CSF antibody HM7/7.7

| | | | | | | | G | P | L | P | G | E | Q | G | D | T | I | G | M-1 | SEQ ID NO: 42 |
|---|---|---|---|---|---|---|---|---|---|---|---|---|---|---|---|---|---|---|---|---|
| | | | S | A | D | P | V | P | G | E | Q | A | A | Q | | | | | M-2 | SEQ ID NO: 43 |
| | | | T | G | V | T | V | P | G | E | Q | A | S | S | | | | | M-3 | SEQ ID NO: 44 |
| | | | | P | P | D | G | I | P | G | E | Q | N | T | G | | | | M-4 | SEQ ID NO: 45 |
| | R | E | D | V | L | T | L | P | G | E | Q | G | | | | | | | M-5 | SEQ ID NO: 46 |
| | S | P | G | P | W | L | A | P | G | E | Q | D | | | | | | | M-6 | SEQ ID NO: 47 |
| | S | P | G | P | W | L | A | P | G | E | Q | D | | | | | | | M-7 | SEQ ID NO: 48 |

| | | | | V | D | S | R | M | P | G | M | Q | A | Q | T | | | | M-8 | SEQ ID NO: 49 |
|---|---|---|---|---|---|---|---|---|---|---|---|---|---|---|---|---|---|---|---|---|
| | | | | G | A | T | S | L | P | G | Q | Q | V | H | R | | | | M-9 | SEQ ID NO: 50 |
| S | G | T | V | H | S | V | V | P | G | T | Q | | | | | | | | M-10 | SEQ ID NO: 51 |
| | P | T | T | E | G | E | L | P | G | V | Q | V | | | | | | | M-11 | SEQ ID NO: 52 |
| | | | G | H | E | A | I | P | G | H | Q | D | Q | L | | | | | M-12 | SEQ ID NO: 53 |
| | | P | R | P | Q | L | I | P | G | T | Q | L | L | | | | | | M-13 | SEQ ID NO: 54 |
| | | | M | E | L | D | I | P | G | D | Q | Q | L | H | | | | | M-14 | SEQ ID NO: 55 |
| | | | | | E | A | V | P | G | S | Q | R | N | I | H | G | | | M-15 | SEQ ID NO: 56 |
| | P | G | G | P | P | L | P | G | I | Q | P | G | | | | | | | M-16 | SEQ ID NO: 57 |
| | R | W | R | E | G | V | P | G | M | Q | G | G | | | | | | | M-17 | SEQ ID NO: 58 |
| | L | S | H | L | H | I | P | G | S | Q | E | N | | | | | | | M-18 | SEQ ID NO: 59 |
| | | | | F | E | D | L | P | G | Y | Q | R | N | R | E | | | | M-19 | SEQ ID NO: 60 |
| | | | D | R | E | T | P | P | G | V | Q | G | D | V | | | | | M-20 | SEQ ID NO: 61 |

TABLE 2-continued

The sequences of the "hits" for the M-CSF antibody HM7/7.7

| | | | | | | | | | | | | | | | |
|---|---|---|---|---|---|---|---|---|---|---|---|---|---|---|---|
| K | Q | A | V | I | P | A | T | Q | H | S | V | | M-21 | SEQ ID NO: 62 |
| Q | A | V | L | G | P | Q | M | D | Q | G | I | | M-22 | SEQ ID NO: 63 |
| | | | | | | | | | | | | | | | |
| G | E | G | S | S | L | L | P | G | E | Q | P | L | H | T | V | D | M-CSF SEQ ID NO: 64 |

TABLE 3

The sequences of the "hits" for the IL-12 antibody C11.5.14

| | | | | | | | | | | | | | | | | |
|---|---|---|---|---|---|---|---|---|---|---|---|---|---|---|---|---|
| | | | | D | I | V | R | L | R | G | D | K | R | E | F | | 12-1 SEQ ID NO: 65 |
| | | | | | | V | R | V | R | G | D | D | F | E | V | F G | 12-2 SEQ ID NO: 66 |
| | | | A | E | G | I | T | V | R | L | R | V | Q | N | | | 12-3 SEQ ID NO: 67 |
| T | S | N | L | F | F | E | Q | R | X | R | D | | | | | | 12-4 SEQ ID NO: 68 |
| | | | | | | E | V | I | R | G | D | Q | R | A | R H S | | 12-5 SEQ ID NO: 69 |
| | | | L | L | G | S | V | V | R | G | T | K | P | D | | | 12-6 SEQ ID NO: 70 |
| | | | | | | | | V | R | G | E | I | R | D | R R E Q G | | 12-7 SEQ ID NO: 71 |

T L S A E R V R G D N K E Y E    p40 of hIL-12 SEQ ID NO: 72

A clear consensus binding sequence can be identified for each of the three monoclonal antibodies. Furthermore, in each case the consensus can be readily aligned with a contiguous sequence present on the original antigen. In the case of HIL8-NR7, the mapped epitope appears to be the sequence -H18-P-K-F21- found in the 72 amino-acid form of human IL-8 (Table 1) (SEQ ID NO:41); for HM7/7.7 the epitope suggested is -L203-P-G-E-Q207- present in human M-CSF (Table 2) (SEQ ID NO:64); and for C11.5.14 the probable epitope maps to -R157-V-R-G-D161-located in the p40 subunit of the human IL-12 heterodimer (Table 3) (SEQ ID NO:72). Individual amino-acid residues within the consensus regions are conserved to different degrees, possibly indicating different contributions towards binding. For example, the consensus sequence for the epitope of the antibody against M-CSF (Table 2) is X1-P-G-X2-Q (SEQ ID NO:74), where position X1 is almost always an aliphatic hydrophobic residue, whereas a wider variety of residues is allowed at X2 with glutamate preferred. Residues within the consensus sequences of the epitopes for the other two antibodies also exhibit variable degrees of conservation (Tables 1 and 3).

The highly conserved "core" region of each consensus sequence is 3 to 5 residues long. Positional preference of these "core" consensus residues within the dodecapeptide sequence varies. For example, the core sequence mapped for the epitope for the antibody against M-CSF appears to favor the carboxyl-end of the dodecapeptide (Table 2). Such positional preference might be a reflection of structural constraints on the inserted peptide imposed by thioredoxin which might limit the available positions for antibody binding. Because the antibody used in the case of HIL-8-NR7 is a neutralizing antibody, the peptides which bind to this antibody, e.g., SEQ ID NOS:6–40, or the consensus sequence (SEQ ID NO:73) are expected to be useful as IL-8 effector molecules.

Confirmation of Antibody Epitopes

Further experiments are performed to confirm that the consensus sequences suggested by the "hits" are the true antibody epitopes. The consensus sequence derived using the anti-IL-8 antibody HILS-NR7 was H-X-K-F (SEQ ID NO:73), matching residues 18 to 21 in human IL-8. Since in the FLITRX-peptides selected by this antibody, the histidine and phenylalanine residues are highly conserved, they are probably important for binding (Table 1). To test this, His18 and Phe21 in IL-8 are mutated both individually and together. Among the routants tested, all of the double mutants, and one single mutant F21D, completely abolish antibody binding. The single mutants F21S, F21A and H18D show greatly reduced affinity. Only one mutant, H18A, shows an ability to bind HIL8-NR7 that is close to that observed for wild-type IL-8. These results unequivocally confirm that the FLITRX screen maps the epitope of HILS-NR7.

For the antibody C11.5.14, recombinant human IL-12 (a heterodimer of p35 and p40 subunits, produced for this purpose in E. coli) is run on a reducing SDS-polyacrylamide gel and probed by Western blot. The results show that the p40 subunit of IL-12, and not p35, are recognized by the antibody. This is consistent with the FLITRX experiments, where it is found that the -R-V-R-G-D- (SEQ ID NO:75) consensus sequence derived from the "hits" is present in p40. A similar Western blot performed using the antibody HM7/7.7 on two separate forms of human M-CSF, one full length (amino acids 1–223) and a truncated form (amino acids 1–163), shows that although the full-length M-CSF reacts with the antibody, a truncated fragment does not. Again, this supports the epitope assignment given by the FLITRX results. The N-terminal M-CSF fragment is missing the consensus sequence found by the screen, -L-P-G-E-Q- (SEQ ID NO:64 and SEQ ID NO:74), which lies between residues 203 and 207 of M-CSF.

EXAMPLE 5

Valency Effects in FLITRX Screens

Construction of Dimer Forms of Thioredoxin Carrying Dodecamer Peptide Inserts in the Active-Site Loop Peptides are displayed by the FLITRX system in a multivalent context, i.e., for each flagellum, numerous copies of the peptide are available for binding. It is possible to study the effects of valency on the strength of specific binding to a target protein, and also to confirm that peptides inserted into FLITRX and native thioredoxin active-site loops are conformationally equivalent. This is done by constructing fusion genes comprising "hit" sequences, as well as those comprising non-specific peptides. For example, several "hit" peptide sequences from the IL-8 antibody screen are individually inserted into one or both of the active-site loops of a covalent thioredoxin/thioredoxin dimer. A non-specific peptide is one of comparable length to the "test" peptide and which does not react with the antibody being studied.

Briefly, PCR reactions are performed, using the "hit" FLITRXPEP plasmids as templates, to generate fragments encoding entire thioredoxin regions, including peptide inserts. Restriction sites are incorporated, as is known to one skilled in the art, into the primers so that the PCR products can be easily fused together as modules. Both mono- and di-valent constructs consist of in-frame fusions of two complete peptide-containing thioredoxin domains connected by a -GSGSG-linker. This linker helps reduce possible steric hindrances. The only difference between mono- and divalent species is that the monovalent constructs have a non-specific peptide (-PEQGQRRIGVERGG-) (SEQ ID NO:5) inserted in the first thioredoxin module and the specific peptide of interest in the second thioredoxin module, while the divalent constructs carry the peptide of interest in both modules. These constructs are expressed in G1724 as described, and are screened for binding affinity to the anti-IL-8 antibody, HIL-8-NR7 by Western Blot. Certain peptides, for example 8-4 and 8-5 of Table 1 (SEQ ID NOS: 9 and 10) bind antibody weakly in the monovalent constructs, but exhibit much stronger binding in the divalent constructs. Other peptides bind antibody strongly in both monovalent and divalent constructs, e.g., peptides 8-11 and 8-20 (SEQ ID NOS: 10 and 25). These results clearly demonstrate that valency effects do occur in FLITRX screens, and that peptides selected in these screens exhibit a range of binding affinities, and that the binding affinities can be distinguished.

EXAMPLE 6

Use of FLITRX Methodology to Study Other Interactions

Example 4 illustrates the use of FLITRX screens to map antibody epitopes. The method can also be used to map other protein/protein interactions of interest. Examples of appropriate targets for FLITRX screens include, but are not limited to, hormone receptor molecules such as the IL-6 receptor, the IL-I receptor, gp130 or the TGF-β receptor family. The hormones which are ligands to these receptors are also targets for FLITRX screens. Peptides selected from such screens may prove useful as antagonists or agonists.

Either component of other pairs of interacting molecules are also useful targets for FLITRX screens, for example, transcriptional factors; enzymes such as protein kinases, protein phosphostases and proteases; as well as enzyme substrates and co-factors. Major histocompatibility antigens are also target molecules which can be studied using the methods and reagents of the present invention. Moreover, purified proteins can be used as targets for FLITRX screens according to this invention, either in free solution or immobilized onto a solid support. Alternatively, whole cells having candidate interactor proteins on their surface can be used as targets.

EXAMPLE 7

Use of Methodology in Immunotherapy

The host cells of the invention can function much like an adjuvant. For example, the individual "hits" from selections on target molecules can be used for immunization in the form of attenuated whole cells expressing the antigen, or in the form of purified intact or truncated FLITRXPEP protein. Because flagellates are known to provoke strong immune responses, in part due to the immunogenicity of flagellin-like proteins, the protocols described above increase the chances of obtaining the desired antibodies against the peptide inserts in FLITRX.

As the "hit" peptides mimic the structural features on its cognate ligand recognized by the target molecule, immune responses to these peptides, or the consensus sequence thereof, can block the interaction between the target molecule and its cognate ligand, i.e., the structural features represented by the hits. This is the foundation of immunotherapy based on the invention.

While the present invention has been described in terms of specific methods and compositions, it is understood that variations and modifications will occur to those skilled in the art upon consideration of the present invention. Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed is:

1. A DNA comprising a first DNA encoding a thioredoxin-like sequence fused in-frame to a second DNA encoding a flagellin-like sequence, wherein said thioredoxin-like sequence is inserted into a domain of said flagellin-like sequence which is dispensable for flagellar function, and wherein said DNA encodes a protein which assembles into an exterior organelle.

2. The DNA of claim 1, further comprising a third DNA encoding a peptide, wherein said third DNA is fused in frame with the first DNA encoding a thioredoxin-like sequence wherein the peptide encoded by said third DNA is located within the active site loop of said thioredoxin-like sequence.

3. The DNA of claim 2, further comprising a fourth DNA fused in-frame encoding a linker.

4. The DNA of claim 2, further comprising a fifth DNA fused in-frame encoding a cleavage site.

5. The DNA of claim 2, wherein said peptide encoded by said third DNA sequence comprises 1 to 60 amino acids.

6. The DNA of claim 1, wherein said DNA encoding a thioredoxin-like sequence encodes a protein that:

i) has a three-dimensional structure substantially similar to E. coli thioredoxin and, ii) contains an active-site loop functionally and structurally equivalent to the double cysteine-containing active-site loop of E. coli thioredoxin.

7. The DNA of claim 1, wherein said DNA encoding a thioredoxin-like sequence comprises a DNA sequence selected from the group consisting of the E. coli thioredoxin; human thioredoxin, glutaredoxin; the thioredoxin-like domains of protein disulfide isomerase, form 1 phosphoinositide specific phospholipase C; and ERp72; and E. coli dsbA.

8. A DNA comprising the sequence of SEQ ID NO:76 (FIG. 1).

9. A DNA comprising a DNA encoding SEQ ID NO:77 (FIG. 1).

10. A DNA, free of homologous chromosomal DNA, comprising a DNA encoding a member selected from the group consisting of SEQ ID NOS: 6–29, 31–40, 42–47, 49–63 and 65–71.

11. A peptide comprising an amino acid sequence selected form the group consisting of SEQ ID NOS: 6–29 and 31–40.

12. A host cell transformed with a DNA of claim 1.

13. A host cell transformed with a DNA of claim 2.

14. A host cell transformed with a DNA of claim 3.

15. A host cell transformed with a DNA of claim 2 and wherein said peptide expression product is displayed on the exterior of said host cell.

16. The host cell of claim 13, wherein said host cell is a bacterium.

17. The host cell of claim 13, wherein said host cell is a flagellate.

18. The host cell of claim 13, wherein said host cell is non-motile prior to transformation.

19. The host cell of claim 17, wherein said host cell is flagellin negative prior to transformation.

20. The host cell of claim 17, wherein said flagellate is a member selected from the group consisting of *Escherichia coli*, *Caulobacter crescentus* and *Bacillus subtilus*.

21. The host cell of claim 15, which is *E. coli*.

22. A protein expressed by the DNA of claim 1.

23. A protein expressed by the DNA of claim 2.

24. A protein expressed by the DNA of claim 3.

25. An immunogenic peptide comprising the expression product of claim 2.

26. An immunogenic cell comprising the host cell of claim 13.

27. A kit comprising a library of FLITRXPEP constructs containing the DNA of claim 2, wherein the thioredoxin like sequence is the trxA gene of *E. coli*, the flagellin like sequence is the fliC gene of *E. coli*, and the third DNA encoding a peptide epitope is inserted into the region of the trxA gene encoding the active loop.

28. The kit of claim 27, further comprising a host cell of claim 13.

* * * * *

SEQUENCE LISTING ( 1 ) GENERAL INFORMATION:

( i i i ) NUMBER OF SEQUENCES: 76

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Gln Pro Phe Glu Asp Phe Arg Ile Ser Gln Glu His Leu Ala Asp His
1               5                   10                  15

Phe Asp Gly Arg
            20

( 2 ) INFORMATION FOR SEQ ID NO:3:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:3:

GACTGACTGG TCCGNNNNNN NNNNNNNNNN NNNNNNNNNN NNNNNNNNNN GGTCCTCAGT    60

CAGTCAG    67

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CTGACTGACT GAGGACC    17

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

Pro Glu Gln Gly Gln Arg Arg Ile Gly Val Glu Arg Gly Gly
1               5                   10

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:6:

Val Gly Asn Thr His Gly Arg His Pro Lys Phe Gly
1               5                   10

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:7:

Trp His Pro Lys Phe Ser Leu Thr Arg Gly Leu Asn
1               5                   10

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

His Pro Lys Phe Tyr Arg Met Ile Gly Leu Glu Asp
1               5                   10

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

Thr Leu His Pro Lys Phe Ser Ile Gly Arg Gln Gly
1               5                   10

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:10:

```
Gly Val Gly Glu Val His Pro Lys Phe Leu Val Arg
1               5                   10
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:11:

```
Ser Thr Gly Gln His Arg Lys Phe Asp Leu Gly Arg
1               5                   10
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:12:

```
Arg Val Asp Ala Pro His Arg Lys Phe Met Arg Gly
1               5                   10
```

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:13:

```
Lys Val His Arg Lys Phe Gly Ser Phe Gly Arg Ser
1               5                   10
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:14:

```
    Ile  Pro  Asn  Thr  Ala  His  Arg  Lys  Phe  Pro  Asp  Asp
    1                   5                        10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:15:

```
    Ser  Lys  Gly  Pro  His  Lys  Lys  Phe  Gly  Val  Tyr  Ala
    1                   5                        10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:16:

```
    Arg  Pro  Ile  Pro  His  Lys  Lys  Phe  Arg  Tyr  Thr  Gly
    1                   5                        10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:17:

```
    Gly  Ala  His  Asp  Lys  Phe  Arg  Arg  Ala  Ser  Arg  Ile
    1                   5                        10
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:18:

```
Lys  Trp  Arg  Asp  His  Asp  Lys  Phe  Ser  Thr  Arg  Asn
1                   5                        10
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:19:

```
Ser  Lys  Gly  Arg  Pro  Asn  Thr  Val  His  Ser  Lys  Phe
1                   5                        10
```

(2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:20:

```
Lys  Ile  Phe  Glu  Gly  Arg  Val  His  Thr  Lys  Phe  Ile
1                   5                        10
```

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:21:

```
Tyr  Gly  Leu  Gln  Ile  Pro  His  Asn  Lys  Phe  Ser  Arg
1                   5                        10
```

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Gly  Asp  Ser  Asp  Asn  Arg  Met  His  Met  Lys  Phe  Arg
1                   5                        10
```

( 2 ) INFORMATION FOR SEQ ID NO:23:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:23:

```
Val Ala Asn His Arg Lys Phe Ile Gly Leu Gly Gln
1               5                   10
```

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:24:

```
Ala Asn Ile Ala Arg Lys Phe Arg Ala Met Val Glu
1               5                   10
```

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:25:

```
Thr Gly Met Gly Val His Lys Lys Phe Leu Arg Phe
1               5                   10
```

( 2 ) INFORMATION FOR SEQ ID NO:26:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:26:

```
Gly Arg His Gly Gln Ala Val His Ala Lys Phe Ala
1               5                   10
```

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:27:

```
Tyr Arg Ala Arg Glu His Ile His Asp Lys Phe Arg
1               5                   10
```

( 2 ) INFORMATION FOR SEQ ID NO:28:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:28:

```
Ile Pro His Arg Lys Phe Arg Gln Leu Ser Trp Val
1               5                   10
```

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:29:

```
Arg Ala His Ala His Ser Lys Phe Pro Ser Val Glu
1               5                   10
```

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:30:

```
Ser Thr Gly Gln His Arg Lys Phe Asp Leu Gly Arg
1               5                   10
```

( 2 ) INFORMATION FOR SEQ ID NO:31:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:31:

```
Ala  Ser  Leu  Pro  Gly  Pro  Leu  His  Gln  Lys  Phe  Leu
 1                  5                        10
```

( 2 ) INFORMATION FOR SEQ ID NO:32:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:32:

```
Lys  His  Arg  Lys  Phe  Ser  Asn  Val  Ser  Glu  Phe  Met
 1                  5                        10
```

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:33:

```
Val  Ser  Val  His  Ser  Lys  Phe  Ala  Ser  Arg  Lys  Ala
 1                  5                        10
```

( 2 ) INFORMATION FOR SEQ ID NO:34:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:34:

```
Val  Gly  Pro  His  Pro  Lys  His  Arg  Met  Val  Leu  Gly
 1                  5                        10
```

( 2 ) INFORMATION FOR SEQ ID NO:35:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:35:

```
Arg  Gln  Glu  Arg  Leu  Ile  His  Pro  Lys  Tyr  Gly  Ile
 1                    5                        10
```

( 2 ) INFORMATION FOR SEQ ID NO:36:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:36:

```
Gly  Lys  Gly  Glu  Val  His  Arg  Lys  His  Arg  Val  Gly
 1                    5                        10
```

( 2 ) INFORMATION FOR SEQ ID NO:37:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:37:

```
Thr  Ile  His  Arg  Lys  His  Leu  Gln  Arg  Thr  Glu  Gly
 1                    5                        10
```

( 2 ) INFORMATION FOR SEQ ID NO:38:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:38:

```
Gly  Asn  Pro  His  Ala  Lys  Arg  Lys  Gly  Ser  Gln  Met
 1                    5                        10
```

( 2 ) INFORMATION FOR SEQ ID NO:39:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:39:

```
Glu His Arg Pro Asp Gly Tyr His Leu Arg Phe His
1               5                   10
```

( 2 ) INFORMATION FOR SEQ ID NO:40:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:40:

```
Thr Thr Thr Gly Gln Ala Leu Ala Arg Lys Phe Tyr
1               5                   10
```

( 2 ) INFORMATION FOR SEQ ID NO:41:

( i ) SEQUENCE CHARACTERISTICS:
           ( A ) LENGTH: 16 amino acids
           ( B ) TYPE: amino acid
           ( C ) STRANDEDNESS: single
           ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:41:

```
Ile Lys Thr Tyr Ser Lys Pro Phe His Pro Lys Phe Ile Lys Glu Leu
1               5                   10                  15
```

( 2 ) INFORMATION FOR SEQ ID NO:42:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:42:

```
Gly Pro Leu Pro Gly Glu Gln Gly Asp Thr Ile Gly
1               5                   10
```

(2) INFORMATION FOR SEQ ID NO:43:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:43:

Ser Ala Asp Pro Val Pro Gly Glu Gln Ala Ala Gln
  1               5                   10

(2) INFORMATION FOR SEQ ID NO:44:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:44:

Thr Gly Val Thr Val Pro Gly Glu Gln Ala Ser Ser
  1               5                   10

(2) INFORMATION FOR SEQ ID NO:45:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:45:

Pro Pro Asp Gly Ile Pro Gly Glu Gln Asn Thr Gly
  1               5                   10

(2) INFORMATION FOR SEQ ID NO:46:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:46:

Arg Glu Asp Val Leu Thr Leu Pro Gly Glu Gln Gly
  1               5                   10

( 2 ) INFORMATION FOR SEQ ID NO:47:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:47:

```
Ser  Pro  Gly  Pro  Trp  Leu  Ala  Pro  Gly  Glu  Gln  Asp
1                   5                        10
```

( 2 ) INFORMATION FOR SEQ ID NO:48:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:48:

```
Ser  Pro  Gly  Pro  Trp  Leu  Ala  Pro  Gly  Glu  Gln  Asp
1                   5                        10
```

( 2 ) INFORMATION FOR SEQ ID NO:49:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:49:

```
Val  Asp  Ser  Arg  Met  Pro  Gly  Met  Gln  Ala  Gln  Thr
1                   5                        10
```

( 2 ) INFORMATION FOR SEQ ID NO:50:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:50:

```
Gly  Ala  Thr  Ser  Leu  Pro  Gly  Gln  Gln  Val  His  Arg
1                   5                        10
```

( 2 ) INFORMATION FOR SEQ ID NO:51:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:51:

```
Ser Gly Thr Val His Ser Val Val Pro Gly Thr Gln
1               5                   10
```

( 2 ) INFORMATION FOR SEQ ID NO:52:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:52:

```
Pro Thr Thr Glu Gly Glu Leu Pro Gly Val Gln Val
1               5                   10
```

( 2 ) INFORMATION FOR SEQ ID NO:53:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:53:

```
Gly His Glu Ala Ile Pro Gly His Gln Asp Gln Leu
1               5                   10
```

( 2 ) INFORMATION FOR SEQ ID NO:54:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:54:

```
Pro Arg Pro Gln Leu Ile Pro Gly Thr Gln Leu Leu
1               5                   10
```

( 2 ) INFORMATION FOR SEQ ID NO:55:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:55:

```
Met  Glu  Leu  Asp  Ile  Pro  Gly  Asp  Gln  Gln  Leu  His
1                  5                          10
```

( 2 ) INFORMATION FOR SEQ ID NO:56:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:56:

```
Glu  Ala  Val  Pro  Gly  Ser  Gln  Arg  Asn  Ile  His  Gly
1                  5                          10
```

( 2 ) INFORMATION FOR SEQ ID NO:57:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:57:

```
Pro  Gly  Gly  Pro  Pro  Leu  Pro  Gly  Ile  Gln  Pro  Gly
1                  5                          10
```

( 2 ) INFORMATION FOR SEQ ID NO:58:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:58:

```
Arg  Trp  Arg  Glu  Gly  Val  Pro  Gly  Met  Gln  Gly  Gly
1                  5                          10
```

( 2 ) INFORMATION FOR SEQ ID NO:59:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:59:

```
Leu  Ser  His  Leu  His  Ile  Pro  Gly  Ser  Gln  Glu  Asn
1                   5                             10
```

( 2 ) INFORMATION FOR SEQ ID NO:60:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

```
Phe  Glu  Asp  Leu  Pro  Gly  Tyr  Gln  Arg  Asn  Arg  Glu
1                   5                             10
```

( 2 ) INFORMATION FOR SEQ ID NO:61:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:61:

```
Asp  Arg  Glu  Thr  Pro  Pro  Gly  Val  Gln  Gly  Asp  Val
1                   5                             10
```

( 2 ) INFORMATION FOR SEQ ID NO:62:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:62:

```
Lys  Gln  Ala  Val  Ile  Pro  Ala  Thr  Gln  His  Ser  Val
1                   5                             10
```

( 2 ) INFORMATION FOR SEQ ID NO:63:

( i ) SEQUENCE CHARACTERISTICS:
        ( A ) LENGTH: 12 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:63:

```
Gln  Ala  Val  Leu  Gly  Pro  Gln  Met  Asp  Gln  Gly  Ile
1              5                        10
```

(2) INFORMATION FOR SEQ ID NO:64:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:64:

```
Gly  Glu  Gly  Ser  Ser  Leu  Leu  Pro  Gly  Glu  Gln  Pro  Leu  His  Thr  Val
1              5                        10                       15
Asp  Met  Cys  Ser  Phe
              20
```

(2) INFORMATION FOR SEQ ID NO:65:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:65:

```
Asp  Ile  Val  Arg  Leu  Arg  Gly  Asp  Lys  Arg  Glu  Phe
1              5                        10
```

(2) INFORMATION FOR SEQ ID NO:66:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:66:

```
Val  Arg  Val  Arg  Gly  Asp  Asp  Phe  Glu  Val  Phe  Gly
1              5                        10
```

(2) INFORMATION FOR SEQ ID NO:67:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:67:

```
Ala  Glu  Gly  Ile  Thr  Val  Arg  Leu  Arg  Val  Gln  Asn
1                  5                        10
```

( 2 ) INFORMATION FOR SEQ ID NO:68:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:68:

```
Thr  Ser  Asn  Leu  Phe  Phe  Glu  Gln  Arg  Xaa  Arg  Asp
1                  5                        10
```

( 2 ) INFORMATION FOR SEQ ID NO:69:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:69:

```
Glu  Val  Ile  Arg  Gly  Asp  Gln  Arg  Ala  Arg  His  Ser
1                  5                        10
```

( 2 ) INFORMATION FOR SEQ ID NO:70:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:70:

```
Leu  Leu  Gly  Ser  Val  Val  Arg  Gly  Thr  Lys  Pro  Asp
1                  5                        10
```

( 2 ) INFORMATION FOR SEQ ID NO:71:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:71:

```
Val  Arg  Gly  Glu  Ile  Arg  Asp  Arg  Arg  Glu  Gln  Gly
1                  5                            10
```

( 2 ) INFORMATION FOR SEQ ID NO:72:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:72:

```
Thr  Leu  Ser  Ala  Glu  Arg  Val  Arg  Gly  Asp  Asn  Lys  Glu  Tyr  Glu
1                  5                            10                           15
```

( 2 ) INFORMATION FOR SEQ ID NO:73:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:73:

```
His  Xaa  Lys  Phe
1
```

( 2 ) INFORMATION FOR SEQ ID NO:74:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:74:

```
Xaa  Pro  Gly  Xaa  Gln
1                  5
```

( 2 ) INFORMATION FOR SEQ ID NO:75:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:75:

Arg Val Arg Gly Asp
1               5

( 2 ) INFORMATION FOR SEQ ID NO:76:

( i ) SEQUENCE CHARACTERISTICS:
    ( A ) LENGTH: 4969 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 2706..4206

( x i ) SEQUENCE DESCRIPTION: SEQ ID NO:76:

| | | | | | |
|---|---|---|---|---|---|
| GACGAAAGGG | CCTCGTGATA | CGCCTATTTT | TATAGGTTAA | TGTCATGATA | ATAATGGTTT | 60 |
| CTTAGACGTC | AGGTGGCACT | TTTCGGGGAA | ATGTGCGCGG | AACCCCTATT | TGTTTATTTT | 120 |
| TCTAAATACA | TTCAAATATG | TATCCGCTCA | TGAGACAATA | ACCCTGATAA | ATGCTTCAAT | 180 |
| AATATTGAAA | AAGGAAGAGT | ATGAGTATTC | AACATTTCCG | TGTCGCCCTT | ATTCCCTTTT | 240 |
| TTGCGGCATT | TTGCCTTCCT | GTTTTTGCTC | ACCCAGAAAC | GCTGGTGAAA | GTAAAAGATG | 300 |
| CTGAAGATCA | GTTGGGTGCA | CGAGTGGGTT | ACATCGAACT | GGATCTCAAC | AGCGGTAAGA | 360 |
| TCCTTGAGAG | TTTTCGCCCC | GAAGAACGTT | TTCCAATGAT | GAGCACTTTT | AAAGTTCTGC | 420 |
| TATGTGGCGC | GGTATTATCC | CGTATTGACG | CCGGGCAAGA | GCAACTCGGT | CGCCGCATAC | 480 |
| ACTATTCTCA | GAATGACTTG | GTTGAGTACT | CACCAGTCAC | AGAAAAGCAT | CTTACGGATG | 540 |
| GCATGACAGT | AAGAGAATTA | TGCAGTGCTG | CCATAACCAT | GAGTGATAAC | ACTGCGGCCA | 600 |
| ACTTACTTCT | GACAACGATC | GGAGGACCGA | AGGAGCTAAC | CGCTTTTTTG | CACAACATGG | 660 |
| GGGATCATGT | AACTCGCCTT | GATCGTTGGG | AACCGGAGCT | GAATGAAGCC | ATACCAAACG | 720 |
| ACGAGCGTGA | CACCACGATG | CCTGTAGCAA | TGGCAACAAC | GTTGCGCAAA | CTATTAACTG | 780 |
| GCGAACTACT | TACTCTAGCT | TCCCGGCAAC | AATTAATAGA | CTGGATGGAG | GCGGATAAAG | 840 |
| TTGCAGGACC | ACTTCTGCGC | TCGGCCCTTC | CGGCTGGCTG | GTTATTGCT | GATAAATCTG | 900 |
| GAGCCGGTGA | GCGTGGGTCT | CGCGGTATCA | TTGCAGCACT | GGGGCCAGAT | GGTAAGCCCT | 960 |
| CCCGTATCGT | AGTTATCTAC | ACGACGGGGA | GTCAGGCAAC | TATGGATGAA | CGAAATAGAC | 1020 |
| AGATCGCTGA | GATAGGTGCC | TCACTGATTA | AGCATTGGTA | ACTGTCAGAC | CAAGTTTACT | 1080 |
| CATATATACT | TTAGATTGAT | TTAAAACTTC | ATTTTTAATT | TAAAAGGATC | TAGGTGAAGA | 1140 |
| TCCTTTTTGA | TAATCTCATG | ACCAAAATCC | CTTAACGTGA | GTTTTCGTTC | CACTGAGCGT | 1200 |
| CAGACCCCGT | AGAAAAGATC | AAAGGATCTT | CTTGAGATCC | TTTTTTTCTG | CGCGTAATCT | 1260 |

```
GCTGCTTGCA AACAAAAAAA CCACCGCTAC CAGCGGTGGT TTGTTTGCCG GATCAAGAGC   1320
TACCAACTCT TTTTCCGAAG GTAACTGGCT TCAGCAGAGC GCAGATACCA AATACTGTCC   1380
TTCTAGTGTA GCCGTAGTTA GGCCACCACT TCAAGAACTC TGTAGCACCG CCTACATACC   1440
TCGCTCTGCT AATCCTGTTA CCAGTGGCTG CTGCCAGTGG CGATAAGTCG TGTCTTACCG   1500
GGTTGGACTC AAGACGATAG TTACCGGATA AGGCGCAGCG GTCGGGCTGA ACGGGGGGTT   1560
CGTGCACACA GCCCAGCTTG GAGCGAACGA CCTACACCGA ACTGAGATAC CTACAGCGTG   1620
AGCATTGAGA AAGCGCCACG CTTCCCGAAG GGAGAAAGGC GGACAGGTAT CCGGTAAGCG   1680
GCAGGGTCGG AACAGGAGAG CGCACGAGGG AGCTTCCAGG GGGAAACGCC TGGTATCTTT   1740
ATAGTCCTGT CGGGTTTCGC CACCTCTGAC TTGAGCGTCG ATTTTGTGA TGCTCGTCAG   1800
GGGGGCGGAG CCTATGGAAA AACGCCAGCA ACGCGGCCTT TTACGGTTC CTGGCCTTTT   1860
GCTGGCCTTT TGCTCACATG TTCTTTCCTG CGTTATCCCC TGATTCTGTG GATAACCGTA   1920
TTACCGCCTT TGAGTGAGCT GATACCGCTC GCCGCAGCCG AACGACCGAG CGCAGCGAGT   1980
CAGTGAGCGA GGAAGCGGAA GAGCGCCCAA TACGCAAACC GCCTCTCCCC GCGCGTTGGC   2040
CGATTCATTA ATGCAGAATT GATCTCTCAC CTACCAAACA ATGCCCCCT GCAAAAAATA   2100
AATTCATATA AAAACATAC AGATAACCAT CTGCGGTGAT AAATTATCTC TGGCGGTGTT   2160
GACATAAATA CCACTGGCGG TGATACTGAG CACATCAGCA GGACGCACTG ACCACCATGA   2220
AGGTGACGCT CTTAAAAATT AAGCCCTGAA GAAGGGCAGC ATTCAAAGCA GAAGGCTTTG   2280
GGGTGTGTGA TACGAAACGA AGCATTGGCC GTAAGTGCGA TTCCGGATTA GCTGCCAATG   2340
TGCCAATCGC GGGGGGTTTT CGTTCAGGAC TACAACTGCC ACACACCACC AAAGCTAACT   2400
GACAGGAGAA TCCAGATGGA TGCACAAACA CGCCGCCGCG AACGTCGCGC AGAGAAACAG   2460
GCTCAATGGA AAGCAGCAAA TCCCCTGTTG GTTGGGGTAA GCGCAAAACC AGTTCCGAAA   2520
GATTTTTTTA ACTATAAACG CTGATGGAAG CGTTTATGCG GAAGAGGTAA AGCCCTTCCC   2580
GAGTAACAAA AAAACAACAG CATAAATAAC CCCGCTCTTA CACATTCCAG CCCTGAAAAA   2640
GGGCATCAAA TTAAACCACA CCTATGGTGT AGTAATCAAC GACTTGCAAT ATAGGATAAC   2700
     GAATC ATG GCA CAA GTC ATT AAT ACC AAC AGC CTC TCG CTG ATC ACT     2747
           Met Ala Gln Val Ile Asn Thr Asn Ser Leu Ser Leu Ile Thr
             1               5                  10

CAA AAT AAT ATC AAC AAG AAC CAG TCT GCG CTG TCG AGT TCT ATC GAG       2795
Gln Asn Asn Ile Asn Lys Asn Gln Ser Ala Leu Ser Ser Ser Ile Glu
 15              20                  25                  30

CGT CTG TCT TCT GGC TTG CGT ATT AAC AGC GCG AAG GAT GAC GCA GCG       2843
Arg Leu Ser Ser Gly Leu Arg Ile Asn Ser Ala Lys Asp Asp Ala Ala
                 35                  40                  45

GGT CAG GCG ATT GCT AAC CGT TTC ACC TCT AAC ATT AAA GGC CTG ACT       2891
Gly Gln Ala Ile Ala Asn Arg Phe Thr Ser Asn Ile Lys Gly Leu Thr
             50                  55                  60

CAG GCG GCC CGT AAC GCC AAC GAC GGT ATC TCC GTT GCG CAG ACC ACC       2939
Gln Ala Ala Arg Asn Ala Asn Asp Gly Ile Ser Val Ala Gln Thr Thr
         65                  70                  75

GAA GGC GCG CTG TCC GAA ATC AAC AAC AAC TTA CAG CGT GTG CGT GAA       2987
Glu Gly Ala Leu Ser Glu Ile Asn Asn Asn Leu Gln Arg Val Arg Glu
     80                  85                  90

CTG ACG GTA CAG GCC ACT ACC GGT ACT AAC TCT GAG TCT GAT CTG TCT       3035
Leu Thr Val Gln Ala Thr Thr Gly Thr Asn Ser Glu Ser Asp Leu Ser
 95                 100                 105                 110

TCT ATC CAG GAC GAA ATT AAA TCC CGT CTG GAT GAA ATT GAC CGC GTA       3083
Ser Ile Gln Asp Glu Ile Lys Ser Arg Leu Asp Glu Ile Asp Arg Val
                115                 120                 125
```

| | | | | | | | | | | | | | | | | |
|---|---|---|---|---|---|---|---|---|---|---|---|---|---|---|---|---|
| TCT | GGT | CAG | ACC | CAG | TTC | AAC | GGC | GTG | AAC | GTG | CTG | GCA | AAA | AAT | GGC | 3131 |
| Ser | Gly | Gln | Thr | Gln | Phe | Asn | Gly | Val | Asn | Val | Leu | Ala | Lys | Asn | Gly | |
| | | | 130 | | | | 135 | | | | | | 140 | | | |
| TCC | ATG | AAA | ATC | CAG | GTT | GGC | GCA | AAT | GAT | AAC | CAG | ACT | ATC | ACT | ATC | 3179 |
| Ser | Met | Lys | Ile | Gln | Val | Gly | Ala | Asn | Asp | Asn | Gln | Thr | Ile | Thr | Ile | |
| | | 145 | | | | | 150 | | | | | 155 | | | | |
| GAT | CTG | AAG | CAG | ATT | GAT | GCT | AAA | ACT | CTT | GGC | CTT | GAT | GGT | TTT | AGC | 3227 |
| Asp | Leu | Lys | Gln | Ile | Asp | Ala | Lys | Thr | Leu | Gly | Leu | Asp | Gly | Phe | Ser | |
| | 160 | | | | | 165 | | | | | 170 | | | | | |
| GTT | AAA | AAT | AAC | GAT | ACA | GTT | ACC | ACT | AGT | GCT | CCA | GTA | ACT | GCT | TTT | 3275 |
| Val | Lys | Asn | Asn | Asp | Thr | Val | Thr | Thr | Ser | Ala | Pro | Val | Thr | Ala | Phe | |
| 175 | | | | | 180 | | | | | 185 | | | | | 190 | |
| GGT | GCT | ACC | ACC | ACA | AAC | AAT | ATT | AAA | CTT | ACT | GGA | ATT | ACC | CTT | TCT | 3323 |
| Gly | Ala | Thr | Thr | Thr | Asn | Asn | Ile | Lys | Leu | Thr | Gly | Ile | Thr | Leu | Ser | |
| | | | | 195 | | | | 200 | | | | | 205 | | | |
| ACG | GAA | GCA | GCC | ACT | GAT | ACT | GGC | GGA | ACT | AAC | CCA | GCT | TCA | ATT | GAG | 3371 |
| Thr | Glu | Ala | Ala | Thr | Asp | Thr | Gly | Gly | Thr | Asn | Pro | Ala | Ser | Ile | Glu | |
| | | | 210 | | | | | 215 | | | | | 220 | | | |
| GGT | GTT | TAT | ACT | GAT | AAT | GGT | AAT | GAT | TAC | TAT | GCG | AAA | ATC | ACC | GGT | 3419 |
| Gly | Val | Tyr | Thr | Asp | Asn | Gly | Asn | Asp | Tyr | Tyr | Ala | Lys | Ile | Thr | Gly | |
| | | 225 | | | | | 230 | | | | | 235 | | | | |
| GGT | GAT | AAC | GAT | GGT | ATG | AGC | GAT | AAA | ATT | ATT | CAC | CTG | ACT | GAC | GAC | 3467 |
| Gly | Asp | Asn | Asp | Gly | Met | Ser | Asp | Lys | Ile | Ile | His | Leu | Thr | Asp | Asp | |
| | 240 | | | | | 245 | | | | | 250 | | | | | |
| AGT | TTT | GAC | ACG | GAT | GTA | CTC | AAA | GCG | GAC | GGG | GCG | ATC | CTC | GTC | GAT | 3515 |
| Ser | Phe | Asp | Thr | Asp | Val | Leu | Lys | Ala | Asp | Gly | Ala | Ile | Leu | Val | Asp | |
| 255 | | | | | 260 | | | | | 265 | | | | | 270 | |
| TTC | TGG | GCA | GAG | TGG | TGC | GGT | CCG | TGC | AAA | ATG | ATC | GCC | CCG | ATT | CTG | 3563 |
| Phe | Trp | Ala | Glu | Trp | Cys | Gly | Pro | Cys | Lys | Met | Ile | Ala | Pro | Ile | Leu | |
| | | | | 275 | | | | | 280 | | | | | 285 | | |
| GAT | GAA | ATC | GCT | GAC | GAA | TAT | CAG | GGC | AAA | CTG | ACC | GTT | GCA | AAA | CTG | 3611 |
| Asp | Glu | Ile | Ala | Asp | Glu | Tyr | Gln | Gly | Lys | Leu | Thr | Val | Ala | Lys | Leu | |
| | | | 290 | | | | | 295 | | | | | 300 | | | |
| AAC | ATC | GAT | CAA | AAC | CCT | GGC | ACT | GCG | CCG | AAA | TAT | GGC | ATC | CGT | GGT | 3659 |
| Asn | Ile | Asp | Gln | Asn | Pro | Gly | Thr | Ala | Pro | Lys | Tyr | Gly | Ile | Arg | Gly | |
| | | 305 | | | | | 310 | | | | | 315 | | | | |
| ATC | CCG | ACT | CTG | CTG | CTG | TTC | AAA | AAC | GGT | GAA | GTG | GCG | GCA | ACC | AAA | 3707 |
| Ile | Pro | Thr | Leu | Leu | Leu | Phe | Lys | Asn | Gly | Glu | Val | Ala | Ala | Thr | Lys | |
| | 320 | | | | | 325 | | | | | 330 | | | | | |
| GTG | GGT | GCA | CTG | TCT | AAA | GGT | CAG | TTG | AAA | GAG | TTC | CTC | GAC | GCT | AAC | 3755 |
| Val | Gly | Ala | Leu | Ser | Lys | Gly | Gln | Leu | Lys | Glu | Phe | Leu | Asp | Ala | Asn | |
| 335 | | | | | 340 | | | | | 345 | | | | | 350 | |
| CTG | GCC | TGT | GCC | GCC | AGT | TCT | CCA | ACC | GCG | GTC | AAA | CTG | GGC | GGA | GAT | 3803 |
| Leu | Ala | Cys | Ala | Ala | Ser | Ser | Pro | Thr | Ala | Val | Lys | Leu | Gly | Gly | Asp | |
| | | | | 355 | | | | | 360 | | | | | 365 | | |
| GAT | GGC | AAA | ACA | GAA | GTG | GTC | GAT | ATT | GAT | GGT | AAA | ACA | TAC | GAT | TCT | 3851 |
| Asp | Gly | Lys | Thr | Glu | Val | Val | Asp | Ile | Asp | Gly | Lys | Thr | Tyr | Asp | Ser | |
| | | | 370 | | | | | 375 | | | | | 380 | | | |
| GCC | GAT | TTA | AAT | GGC | GGT | AAT | CTG | CAA | ACA | GGT | TTG | ACT | GCT | GGT | GGT | 3899 |
| Ala | Asp | Leu | Asn | Gly | Gly | Asn | Leu | Gln | Thr | Gly | Leu | Thr | Ala | Gly | Gly | |
| | | 385 | | | | | 390 | | | | | 395 | | | | |
| GAG | GCT | CTG | ACT | GCT | GTT | GCA | AAT | GGT | AAA | ACC | ACG | GAT | CCG | CTG | AAA | 3947 |
| Glu | Ala | Leu | Thr | Ala | Val | Ala | Asn | Gly | Lys | Thr | Thr | Asp | Pro | Leu | Lys | |
| | | | 400 | | | | | 405 | | | | | 410 | | | |
| GCG | CTG | GAC | GAT | GCT | ATC | GCA | TCT | GTA | GAC | AAA | TTC | CGT | TCT | TCC | CTC | 3995 |
| Ala | Leu | Asp | Asp | Ala | Ile | Ala | Ser | Val | Asp | Lys | Phe | Arg | Ser | Ser | Leu | |
| 415 | | | | | 420 | | | | | 425 | | | | | 430 | |
| GGT | GCG | GTG | CAA | AAC | CGT | CTG | GAT | TCC | GCG | GTT | ACC | AAC | CTG | AAC | AAC | 4043 |
| Gly | Ala | Val | Gln | Asn | Arg | Leu | Asp | Ser | Ala | Val | Thr | Asn | Leu | Asn | Asn | |
| | | | | 435 | | | | | 440 | | | | | 445 | | |

| | | | | | | | | | | | | | | | | |
|---|---|---|---|---|---|---|---|---|---|---|---|---|---|---|---|---|
| ACC | ACT | ACC | AAC | CTG | TCT | GAA | GCG | CAG | TCC | CGT | ATT | CAG | GAC | GCC | GAC | 4091 |
| Thr | Thr | Thr | Asn<br>450 | Leu | Ser | Glu | Ala | Gln<br>455 | Ser | Arg | Ile | Gln | Asp<br>460 | Ala | Asp | |
| TAT | GCG | ACC | GAA | GTG | TCC | AAT | ATG | TCG | AAA | GCG | CAG | ATC | ATC | CAG | CAG | 4139 |
| Tyr | Ala | Thr<br>465 | Glu | Val | Ser | Asn | Met<br>470 | Ser | Lys | Ala | Gln | Ile<br>475 | Ile | Gln | Gln | |
| GCC | GGT | AAC | TCC | GTG | TTG | GCA | AAA | GCT | AAC | CAG | GTA | CCG | CAG | CAG | GTT | 4187 |
| Ala | Gly<br>480 | Asn | Ser | Val | Leu | Ala<br>485 | Lys | Ala | Asn | Gln | Val<br>490 | Pro | Gln | Gln | Val | |
| CTG | TCT | CTG | CTG | CAG | GGT | T AATCGTTGTA ACCTGATTAA CTGAGACTGA | | | | | | | | | | 4236 |
| Leu | Ser | Leu | Leu | Gln | Gly<br>500 | | | | | | | | | | | |
| 495 | | | | | | | | | | | | | | | | |

```
CGGCAACGCC AAATTGCCTG ATGCGCTGCG CTTATCAGGC TACAAGTTG  AATTGCAATT    4296
TATTGAATTT GCACATTTTT GTAGGCCGGA TAAGGCGTTT ACGCGCATCC GGCAACATAA    4356
AGCGCAATTT GTCAGCAACG TGCTTCCCGC CACCGGCGGG GTTTTTTTCT GCCTGGAATT    4416
TACCTGTAAC CCCCAAATAA CCCCTCATTT CACCCACTAA TCGTCCGATT AAAAACCCTG    4476
CAGAAACGGA TAATCATGCC GATAACTGCT ATAACGCAGG GCTGTTTGAA TTCCCGGGGA    4536
TCCTCTAGAG TCGACCTGCA GGCATGCAAG CTTGGCACTG GCCGTCGTTT TACAACGTCG    4596
TGACTGGGAA AACCCTGGCG TTACCCAACT TAATCGCCTT GCAGCACATC CCCCTTTCGC    4656
CAGCTGGCGT AATAGCGAAG AGGCCCGCAC CGATCGCCCT TCCCAACAGT TGCGCAGCCT    4716
GAATGGCGAA TGGCGCCTGA TGCGGTATTT TCTCCTTACG CATCTGTGCG GTATTTCACA    4776
CCGCATATAT GGTGCACTCT CAGTACAATC TGCTCTGATG CCGCATAGTT AAGCCAGCCC    4836
CGACACCCGC CAACACCCGC TGACGCGCCC TGACGGGCTT GTCTGCTCCC GGCATCCGCT    4896
TACAGACAAG CTGTGACCGT CTCCGGGAGC TGCATGTGTC AGAGGTTTTC ACCGTCATCA    4956
CCGAAACGCG CGA                                                       4969
```

( 2 ) INFORMATION FOR SEQ ID NO:77:

( i ) SEQUENCE CHARACTERISTICS:
        ( A ) LENGTH: 500 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

```
Met Ala Gln Val Ile Asn Thr Asn Ser Leu Ser Leu Ile Thr Gln Asn
 1               5                  10                  15
Asn Ile Asn Lys Asn Gln Ser Ala Leu Ser Ser Ser Ile Glu Arg Leu
                20                  25                  30
Ser Ser Gly Leu Arg Ile Asn Ser Ala Lys Asp Asp Ala Ala Gly Gln
            35                  40                  45
Ala Ile Ala Asn Arg Phe Thr Ser Asn Ile Lys Gly Leu Thr Gln Ala
        50                  55                  60
Ala Arg Asn Ala Asn Asp Gly Ile Ser Val Ala Gln Thr Thr Glu Gly
    65                  70                  75                  80
Ala Leu Ser Glu Ile Asn Asn Asn Leu Gln Arg Val Arg Glu Leu Thr
                85                  90                  95
Val Gln Ala Thr Thr Gly Thr Asn Ser Glu Ser Asp Leu Ser Ser Ile
               100                 105                 110
Gln Asp Glu Ile Lys Ser Arg Leu Asp Glu Ile Asp Arg Val Ser Gly
            115                 120                 125
Gln Thr Gln Phe Asn Gly Val Asn Val Leu Ala Lys Asn Gly Ser Met
```

-continued

```
                130                       135                           140
Lys  Ile  Gln  Val  Gly  Ala  Asn  Asp  Asn  Gln  Thr  Ile  Thr  Ile  Asp  Leu
145                      150                      155                      160
Lys  Gln  Ile  Asp  Ala  Lys  Thr  Leu  Gly  Leu  Asp  Gly  Phe  Ser  Val  Lys
                    165                      170                      175
Asn  Asn  Asp  Thr  Val  Thr  Thr  Ser  Ala  Pro  Val  Thr  Ala  Phe  Gly  Ala
                    180                      185                      190
Thr  Thr  Thr  Asn  Asn  Ile  Lys  Leu  Thr  Gly  Ile  Thr  Leu  Ser  Thr  Glu
               195                      200                 205
Ala  Ala  Thr  Asp  Thr  Gly  Gly  Thr  Asn  Pro  Ala  Ser  Ile  Glu  Gly  Val
          210                      215                 220
Tyr  Thr  Asp  Asn  Gly  Asn  Asp  Tyr  Tyr  Ala  Lys  Ile  Thr  Gly  Gly  Asp
225                      230                      235                      240
Asn  Asp  Gly  Met  Ser  Asp  Lys  Ile  Ile  His  Leu  Thr  Asp  Asp  Ser  Phe
                    245                      250                      255
Asp  Thr  Asp  Val  Leu  Lys  Ala  Asp  Gly  Ala  Ile  Leu  Val  Asp  Phe  Trp
                    260                      265                      270
Ala  Glu  Trp  Cys  Gly  Pro  Cys  Lys  Met  Ile  Ala  Pro  Ile  Leu  Asp  Glu
               275                      280                      285
Ile  Ala  Asp  Glu  Tyr  Gln  Gly  Lys  Leu  Thr  Val  Ala  Lys  Leu  Asn  Ile
290                      295                      300
Asp  Gln  Asn  Pro  Gly  Thr  Ala  Pro  Lys  Tyr  Gly  Ile  Arg  Gly  Ile  Pro
305                      310                      315                      320
Thr  Leu  Leu  Leu  Phe  Lys  Asn  Gly  Glu  Val  Ala  Ala  Thr  Lys  Val  Gly
               325                      330                      335
Ala  Leu  Ser  Lys  Gly  Gln  Leu  Lys  Glu  Phe  Leu  Asp  Ala  Asn  Leu  Ala
               340                      345                      350
Cys  Ala  Ala  Ser  Ser  Pro  Thr  Ala  Val  Lys  Leu  Gly  Gly  Asp  Asp  Gly
          355                      360                      365
Lys  Thr  Glu  Val  Val  Asp  Ile  Asp  Gly  Lys  Thr  Tyr  Asp  Ser  Ala  Asp
     370                      375                      380
Leu  Asn  Gly  Gly  Asn  Leu  Gln  Thr  Gly  Leu  Thr  Ala  Gly  Gly  Glu  Ala
385                      390                      395                      400
Leu  Thr  Ala  Val  Ala  Asn  Gly  Lys  Thr  Thr  Asp  Pro  Leu  Lys  Ala  Leu
                    405                      410                      415
Asp  Asp  Ala  Ile  Ala  Ser  Val  Asp  Lys  Phe  Arg  Ser  Ser  Leu  Gly  Ala
               420                      425                      430
Val  Gln  Asn  Arg  Leu  Asp  Ser  Ala  Val  Thr  Asn  Leu  Asn  Asn  Thr  Thr
          435                      440                      445
Thr  Asn  Leu  Ser  Glu  Ala  Gln  Ser  Arg  Ile  Gln  Asp  Ala  Asp  Tyr  Ala
     450                      455                      460
Thr  Glu  Val  Ser  Asn  Met  Ser  Lys  Ala  Gln  Ile  Ile  Gln  Gln  Ala  Gly
465                      470                      475                      480
Asn  Ser  Val  Leu  Ala  Lys  Ala  Asn  Gln  Val  Pro  Gln  Gln  Val  Leu  Ser
                    485                      490                      495
Leu  Leu  Gln  Gly
               500
```